United States Patent
Lattwein et al.

(10) Patent No.: US 10,802,024 B2
(45) Date of Patent: Oct. 13, 2020

(54) METHOD FOR THE DIAGNOSIS OF BORNAVIRUS INFECTION

(71) Applicant: EUROIMMUN Medizinische Labordiagnostika AG, Luebeck (DE)

(72) Inventors: Erik Lattwein, Luebeck (DE); Wolfgang Meyer, Pansdorf (DE); Wolfgang Schlumberger, Groß Grönau (DE); Julia Janz, Schönberg (DE); Anthonina Ott, Schiphorst (DE); Thomas Scheper, Berkenthin (DE); Jonas Schmidt-Chanasit, Berlin (DE); Dennis Tappe, Hamburg (DE)

(73) Assignee: EUROIMMUN Medizinische Labordiagnostika AG, Luebeck (DE)

( * ) Notice: Subject to any disclaimer, the term of this patent is extended or adjusted under 35 U.S.C. 154(b) by 0 days.

(21) Appl. No.: 16/227,334

(22) Filed: Dec. 20, 2018

(65) Prior Publication Data
US 2019/0204318 A1 Jul. 4, 2019

(30) Foreign Application Priority Data
Dec. 29, 2017 (EP) ..................................... 17211138

(51) Int. Cl.
*G01N 33/569* (2006.01)
*G01N 33/543* (2006.01)

(52) U.S. Cl.
CPC ..... *G01N 33/56983* (2013.01); *G01N 33/543* (2013.01); *G01N 2333/08* (2013.01); *G01N 2469/10* (2013.01)

(58) Field of Classification Search
CPC .... A61K 38/00; G01N 33/08; G01N 2469/10; G01N 33/56983
See application file for complete search history.

(56) References Cited

U.S. PATENT DOCUMENTS

| | | |
|---|---|---|
| 6,403,301 B1 | 6/2002 | Ludwig et al. |
| 9,250,250 B2 | 2/2016 | Dalmau |
| 9,719,993 B2 | 8/2017 | Dalmau |
| 2009/0155261 A1 | 6/2009 | Dalmau |
| 2013/0072582 A1 | 3/2013 | Dalmau |

FOREIGN PATENT DOCUMENTS

| | | |
|---|---|---|
| EP | 2 057 466 | 10/2013 |
| EP | 2 863 231 | 4/2015 |
| EP | 2 905 622 | 8/2015 |
| EP | 3 018 478 | 5/2016 |
| EP | 3 026 434 | 6/2016 |
| EP | 3 101 424 | 12/2016 |
| EP | 2 483 417 | 3/2017 |
| JP | 2002-500363 | 1/2002 |
| JP | H11 180998 | 3/2014 |
| WO | 98/18457 | 5/1998 |
| WO | 98/30238 | 7/1998 |
| WO | 1999/34216 | 7/1999 |
| WO | 2014/041035 | 3/2014 |

OTHER PUBLICATIONS

Hornig, et al., author manuscript, published as: Mol Psychiatry, 2012, 17(5):486-493; DOI:10.1038/mp.2011.179.
Lipkin, et al., Virus Research 2011, 162:162-172.
Zhang, et al., European Journal of Clinical Microbiology & Infectious Diseases, 2014, 33:621-627, (abstract).
Robert Koch Institute, "*Background to the discontinuation of Bornavirus research at the Robert Koch Institute*," May 30, 2007, 5 pp., submitting English-language translation.
Simon, et al., *Clinical Neurology*, 7th edition, 2009, pp. 83-88.
Search Report dated May 4, 2018 in European Application No. 17211138.7 with English translation.
Bloch et al. "*Diagnostic approaches for patients with suspected encephalitis*," Current Infectious Disease Reports, 2007, vol. 9, pp. 315-322.
Bode et al. "*Borna disease virus-specific circulating immune complexes, antigenemia, and free antibodies—the key marker triplet determining infection and prevailing in severe mood disorders*," Molecular Psychiatry (2001), vol. 6, pp. 481-491.
Bourg et al. "*Screening red foxes (Vulpes vulpes) for possible viral causes of encephalitis*," Virology Journal (2016), 13:151, 12 pages. DOI: 10.1186/s12985-016-0608-1.
Hoffmann et al. "A Variegated Squirrel Bornavirus Associated with Fatal Human Encephalitis," New England Journal of Medicine vol. 373, No. 2, Jul. 9, 2015, pp. 154-162. DOI: 10.1056/NEJMoa1415627.
Larkin et al. "*Clustal W and Clustal X version 2.0*," Bioinformatics, vol. 23, No. 21, 2007, pp. 2947-2948. doi: 10.1093/bioinformatics/btm404.
Friedrich Löffler Institute reports on the development of a test for the detection of VSBV-1 (http://www.wir-sind-tierarzt.de/2015/07/bestaetigt-bunthoernchen-uebertragen-bornaviren/, retrieved on Dec. 14, 2017).
Li et al. "*Detection and analysis of Borna disease virus in Chinese patients with neurological disorders*," European Journal of Neurology 2009, vol. 16, pp. 399-403. DOI: 10.IIII/j.1468-1331-2008-02516.x.

(Continued)

*Primary Examiner* — Bao Q Li
(74) *Attorney, Agent, or Firm* — Grüneberg and Myers PLLC

(57) ABSTRACT

A method for diagnosing a limbic encephalitis, PNS, encephaloymyelitis, leukoencephalopathy, retinitis or optic atrophy, includes detecting a bornavirus in a sample, preferably from the group comprising mammalian 2 bornavirus, even more preferably VSBV-1, and mammalian 1 bornavirus, even more preferably BoDV-1; to a carrier containing a means for the capture of an antibody against at least one polypeptide selected from the group of BoDV-1-N, BoDV-1-P, VSBV-N and VSBV-P. A kit contains the carrier and a means for the detection of a captured antibody and a control for the detection of the presence of a sample. The carrier or kit or of a primer can be used for the detection of a bornavirus or a probe can be used for the diagnosis of an encephalitis, for the prognostication of post-transplantation complications, for the monitoring of a therapy of an encephalitis or of post-transplantation complications or for the differentiation between an autoimmune encephalitis and an encephalitis caused by infection.

10 Claims, 6 Drawing Sheets
Specification includes a Sequence Listing.

(56) References Cited

OTHER PUBLICATIONS

Ludlow et al. "*Neurotropic virus infections as the cause of immediate and delayed neuropathology,*" Acta Neuropathol (2016) vol. 131, pp. 159-184. DOI: 10.1007/s00401-015-1511-3.
Matsunaga et al. "*Isotype analysis of human anti-Borna disease virus antibodies in Japanese psychiatric and general population,*" Journal of Clinical Virology vol. 43, (2008), pp. 317-322. DOI: 10.1016/J.JCV.2008.07.011.
Melzer et al. (2015) "*Limbic Encephalitis: Potential Impact of Adaptive Autoimmune Inflammation on Neuronal Circuits of the Amygdala,*" Frontiers in Neurology, vol. 6, Article 171, 10 pages.
Pelay-Gimeno et al. "*Structure-based design of inhibitors of protein-protein interactions: Mimicking peptide binding epitopes,*" Angewandte Chemie Int. Ed., 2015, vol. 54, pp. 8896-8927.
Schlottau et al. "*Veriegated Squirrel Bornavirus 1 in Squirrels, Germany and the Netherlands,*" Emerging infectious Diseases, vol. 23, No. 3, Mar. 2017, pp. 477-481.
Schlottau et al. "*Fatal Encephalitic Borna Disease Virus 1 in Solid-Organ Transplant Recipients,*" New England Journal of Medicine, 379;14, Oct. 4, 2018.
Senzolo et al. "*Neurologic complications after solid organ transplantation,*" Journal compilation © 2008, European Society for Organ Transplantation, vol. 22 (2009), pp. 269-278.
Shahhosseini et al. "*Detection and characterization of a novel rhabdovirus in Aedes cantans mosquitoes and evidence for a mosquito-associated new genus in the family Rhabdoviridae,*" (2017) Infection, Genetics and Evolution, vol. 55 (2017), pp. 260-268.
Shalimar et al. "*Management in Acute Liver Failure,*" Journal of Clinical and Experimental Hepatology, Mar. 2015, vol. 5, No. S1, pp. s104-s115.
Tappe et al. "*Bornavirus Associated with Fatal Human Encephalitis,*" New England Journal of Medicine, vol. 373, No. 19, Nov. 5, 2015, pp. 1880-1881.
Tappe et al. "Fatal limbic encephalitis in a zoo animal caretaker caused by variegates squirrel bornavirus: Zoonotic bornaviruses as occupational risk," manuscript submitted (2018), pp. 65-101.
Q. Teng "Structural Biology: Practical Applications," (2013) Chapter 2, pp. 65-101, Springer+Business Media, New York.
Office Action dated Apr. 7, 2020 in European Application No. 18214997.1 with English translation, 12 pages.
Notice of Preliminary Rejection dated Apr. 6, 2020 in Korean Application No. 10-2018-0164818 with English translation, 21 pages.
Stahl et al., Journal of Neuroimmunology; 2003, 137:67-78.
Office Action dated Jun. 22, 2020 in European Application No. 18 214 997.1 with English translation, 12 pages.
Chong et al., Annals of Neurology, vol. 49, No. 6, Jun. 2001, pp. 810-813.

VSBV-N - 1
VSBV-N - 2
VSBV-N peptide - 1
VSBV-N peptide - 2
VSBV-P - 1
VSBV-P - 2
BoDV-N - 1
BoDV-N - 2
BoDV-P - 1
BoDV-P - 2 incubation control

| d post-Tx (symptoms up from d98) | Et | Ko | BoDV-P 2 | BoDV-P 1 | BoDV-N 2 | BoDV-N 1 | VSBV-P 2 | VSBV-P 1 | VSBV-N 2 | VSBV-N 1 |
|---|---|---|---|---|---|---|---|---|---|---|
| A2 d463 17020361 / 17-25306 Borna/10-27 | | 108 + | 34 (+) | 77 + | 4 n | 8 n | 2 n | 2 n | 10 n | 13 n | 10 n | 22 + |
| A2 d435 17020352 / 17-22480 Borna/14-19 | | 105 + | 37 (+) | 78 + | 2 n | 8 n | 0 n | 5 n | 14 (+) | 19 (+) | 8 n | 19 (+) |
| A1 d382 17013915 / 17-16861 Borna/08-65 | | 94 + | 44 (+) | 92 + | 4 n | 12 n | 1 n | 2 n | 9 n | 21 + | 13 n | 28 + |
| A2 d382 17020358 / 17-16861 control Borna/10-26 | | 106 + | 35 (+) | 80 + | 6 n | 8 n | 5 n | 0 n | 12 n | 19 (+) | 10 n | 28 + |
| A1 d210 17013914 / 16-36042 Borna/08-62 | | 88 + | 51 (+) | 98 + | 3 n | 6 n | 1 n | 1 n | 8 n | 20 (+) | 2 n | 10 n |
| A2 d175 17020350 / 16-31947 Borna/14-18 | | 106 + | 32 (+) | 73 + | 3 n | 8 n | 1 n | 2 n | 15 (+) | 29 + | 3 n | 6 n |
| A2 d135 17020346 / 16-27637 Borna/13-22 | | 107 + | 30 (+) | 72 + | 1 n | 4 n | 1 n | 1 n | 12 n | 20 (+) | 2 n | 4 n |
| A1 d114 17013913 / 16-25371 Borna/08-61 | | 92 + | 16 (+) | 62 + | 2 n | 4 n | 1 n | 1 n | 4 n | 14 (+) | 1 n | 2 n |
| A1 d94 17013912 / 16-23312 Borna/08-60 | | 91 + | 16 (+) | 62 + | 2 n | 4 n | 0 n | 1 n | 4 n | 14 (+) | 1 n | 2 n |
| A1 d84 17013911 / 16-22175 Borna/08-59 | | 88 + | 16 (+) | 62 + | 2 n | 4 n | 1 n | 1 n | 4 n | 14 (+) | 1 n | 1 n |
| A1 d72 17013910 / 16-21069 Borna/08-58 | | 91 + | 1 n | 2 n | 2 n | 4 n | 1 n | 2 n | 7 n | 18 (+) | 1 n | 0 n |

Fig. 6

SEQUENCE LISTING

<160> NUMBER OF SEQ ID NOS: 7

<210> SEQ ID NO 1
<211> LENGTH: 382
<212> TYPE: PRT
<213> ORGANISM: Artificial Sequence
<220> FEATURE:
<223> OTHER INFORMATION: Description of Artificial Sequence: Synthetic
      VSBV-N (40 kDa, His-Tag)

<400> SEQUENCE: 1

```
Met Asn Ile Thr Met Pro Pro Lys Arg Arg Leu Leu Glu Asp Pro Asp
1               5                   10                  15
Val Met Asp Asp Gln Glu Pro Glu Pro Thr Ser Pro Pro Met Pro Lys
            20                  25                  30
Leu Pro Gly Lys Phe Leu Gln Tyr Thr Val Gly Gly Ser Asp Pro His
        35                  40                  45
Pro Gly Ile Gly Glu Glu Lys Asp Ile Lys His Asn Ala Val Ala Leu
    50                  55                  60
Leu Asp Ser Ser Arg Arg Asp Met Phe His Pro Val Thr Pro Ser Leu
65                  70                  75                  80
Val Phe Leu Cys Leu Leu Ile Pro Gly Leu His Ala Ala Phe Leu His
                85                  90                  95
Gly Gly Val Pro Lys Glu Ser Tyr Leu Ser Thr Pro Ile Ser Arg Gly
            100                 105                 110
Glu Gln Thr Phe Val Lys Val Ser Arg Phe Tyr Gly Glu Arg Thr Ala
        115                 120                 125
Ser Arg Glu Leu Thr Glu Leu Glu Ile Ser Ser Ile Phe Asn His Cys
    130                 135                 140
Cys Ser Leu Leu Ile Gly Val Val Ile Gly Ser Ser Ala Lys Ile Arg
145                 150                 155                 160
Ala Gly Ala Glu Gln Ile Lys Lys Arg Phe Lys Thr Leu Met Ala Ser
                165                 170                 175
Leu Asn Arg Pro Ser His Gly Glu Thr Ala Thr Leu Leu Gln Met Phe
            180                 185                 190
Asn Pro His Glu Ala Ile Asp Trp Ile Asn Gly Gln Pro Trp Val Gly
        195                 200                 205
Ser Leu Val Leu Ser Leu Thr Thr Asp Phe Glu Ser Pro Gly Lys
    210                 215                 220
Glu Phe Met Asp Gln Ile Lys Leu Val Ala Ser Tyr Ala Gln Met Thr
225                 230                 235                 240
Thr Tyr Thr Thr Ile Lys Glu Tyr Leu Ala Glu Cys Met Asp Ala Thr
                245                 250                 255
Leu Thr Ile Pro Ala Val Ala His Glu Ile Arg Glu Phe Leu Glu Ile
            260                 265                 270
Ser Ala Lys Leu Lys Asn Glu His Ala Glu Leu Phe Pro Phe Leu Gly
        275                 280                 285
Ala Ile Arg His Pro Asp Ala Ile Lys Leu Ala Pro Arg Ser Phe Pro
    290                 295                 300
Asn Leu Ala Ser Ala Ala Phe Tyr Trp Ser Lys Lys Glu Asn Pro Thr
305                 310                 315                 320
Met Ala Gly Tyr Arg Ala Ser Thr Ile Gln Pro Gly Ala Thr Val Lys
                325                 330                 335
Glu Thr Gln Leu Ala Arg Tyr Arg Arg Arg Glu Val Ser Arg Gly Glu
            340                 345                 350
Asp Gly Ala Glu Leu Ser Gly Glu Ile Ser Asp Ile Met Lys Met Ile
        355                 360                 365
Gly Val Thr Gly Leu Val Leu Glu His His His His His
    370                 375                 380
```

<210> SEQ ID NO 2  
<211> LENGTH: 253  
<212> TYPE: PRT  
<213> ORGANISM: Artificial Sequence

```
<220> FEATURE:
<223> OTHER INFORMATION: Description of Artificial Sequence: Synthetic
      VSBV-N peptide (30 kDa, His-GST-Tag)

<400> SEQUENCE: 2

Met Ser His His His His His His His Met Ser Pro Ile Leu Gly
1               5                   10                  15

Tyr Trp Lys Ile Lys Gly Leu Val Gln Pro Thr Arg Leu Leu Leu Glu
                20                  25                  30

Tyr Leu Glu Glu Lys Tyr Glu His Leu Tyr Glu Arg Asp Glu Gly
            35                  40                  45

Asp Lys Trp Arg Asn Lys Lys Phe Glu Leu Gly Leu Glu Phe Pro Asn
50                  55                  60

Leu Pro Tyr Tyr Ile Asp Gly Asp Val Lys Leu Thr Gln Ser Met Ala
65                  70                  75                  80

Ile Ile Arg Tyr Ile Ala Asp Lys His Asn Met Leu Gly Gly Cys Pro
                85                  90                  95

Lys Glu Arg Ala Glu Ile Ser Met Leu Glu Gly Ala Val Leu Asp Ile
            100                 105                 110

Arg Tyr Gly Val Ser Arg Ile Ala Tyr Ser Lys Asp Phe Glu Thr Leu
        115                 120                 125

Lys Val Asp Phe Leu Ser Lys Leu Pro Glu Met Leu Lys Met Phe Glu
130                 135                 140

Asp Arg Leu Cys His Lys Thr Tyr Leu Asn Gly Asp His Val Thr His
145                 150                 155                 160

Pro Asp Phe Met Leu Tyr Asp Ala Leu Asp Val Val Leu Tyr Met Asp
                165                 170                 175

Pro Met Cys Leu Asp Ala Phe Pro Lys Leu Val Cys Phe Lys Lys Arg
            180                 185                 190

Ile Glu Ala Ile Pro Gln Ile Asp Lys Tyr Leu Lys Ser Ser Lys Tyr
        195                 200                 205

Ile Ala Trp Pro Leu Gln Gly Trp Gln Ala Thr Phe Gly Gly Gly Asp
    210                 215                 220

His Pro Pro Lys Leu Glu Val Leu Phe Gln Gly Pro Ala Met Phe Val
225                 230                 235                 240

Lys Val Ser Arg Phe Tyr Gly Glu Arg Thr Ala Ser Arg
                245                 250

<210> SEQ ID NO 3
<211> LENGTH: 210
<212> TYPE: PRT
<213> ORGANISM: Artificial Sequence
<220> FEATURE:
<223> OTHER INFORMATION: Description of Artificial Sequence: Synthetic
      VSBV-P (23 kDa, His-Tag)

<400> SEQUENCE: 3

Met Ala Ser Arg Pro Ser Ser Leu Val Glu Ser Leu Glu Asp Glu
1               5                   10                  15

Ser Leu Gln Thr Pro Arg Arg Val Arg Ser Arg Ser Pro Arg Pro Lys
                20                  25                  30

Arg Ile Pro Gln Asp Ala Leu Thr Gln Pro Val Asp Arg Leu Leu Lys
            35                  40                  45

Asn Ile Lys Lys Asn Pro Ser Met Ile Ser Asp Pro Glu Gln Arg Thr
        50                  55                  60

Gly Arg Glu Gln Leu Ser Asn Asp Glu Leu Ile Lys Gln Leu Val Thr
65                  70                  75                  80
```

-continued

```
Glu Leu Ala Glu Asn Ser Met Ile Glu Ala Gly Leu Arg Gly Ala
                85                  90                  95

Leu Asp Asp Ile Ser Ser Lys Val Asp Ser Gly Leu Glu Ser Ile Ser
            100                 105                 110

Ser Leu Gln Val Glu Thr Leu Gln Thr Val Gln Lys Thr Asp Tyr Ala
            115                 120                 125

Asp Ser Ile Lys Thr Leu Gly Glu Asn Ile Lys Val Leu Asp Arg Ser
        130                 135                 140

Met Lys Thr Met Met Glu Thr Met Arg Leu Met Met Glu Lys Ile Asp
145                 150                 155                 160

Leu Leu Tyr Ala Ser Thr Ala Ile Gly Gln Ser Asn Thr Pro Met Leu
                165                 170                 175

Pro Ser His Pro Ala Gln Pro Arg Leu Tyr Pro Thr Leu Pro Ser Ala
            180                 185                 190

Pro Thr Ala Asp Glu Trp Asp Ile Leu Pro Leu Glu His His His
        195                 200                 205

His His
    210

<210> SEQ ID NO 4
<211> LENGTH: 382
<212> TYPE: PRT
<213> ORGANISM: Artificial Sequence
<220> FEATURE:
<223> OTHER INFORMATION: Description of Artificial Sequence: Synthetic
      BoDV-N (40 kDa, His-Tag)

<400> SEQUENCE: 4

Met As

-continued

```
Glu Phe Met Asp Gln Ile Lys Leu Val Ala Ser Tyr Ala Gln Met Thr
225                 230                 235                 240

Thr Tyr Thr Thr Ile Lys Glu Tyr Leu Ala Glu Cys Met Asp Ala Thr
                245                 250                 255

Leu Thr Ile Pro Val Val Ala Tyr Glu Ile Arg Asp Phe Leu Glu Val
            260                 265                 270

Ser Ala Lys Leu Lys Glu Glu His Ala Asp Leu Phe Pro Phe Leu Gly
        275                 280                 285

Ala Ile Arg His Pro Asp Ala Ile Lys Leu Ala Pro Arg Ser Phe Pro
    290                 295                 300

Asn Leu Ala Ser Ala Ala Phe Tyr Trp Ser Lys Lys Glu Asn Pro Thr
305                 310                 315                 320

Met Ala Gly Tyr Arg Ala Ser Thr Ile Gln Pro Gly Ala Ser Val Lys
                325                 330                 335

Glu Thr Gln Leu Ala Arg Tyr Arg Arg Arg Glu Ile Ser Arg Gly Glu
            340                 345                 350

Asp Gly Ala Glu Leu Ser Gly Glu Val Ser Ala Ile Met Lys Met Ile
        355                 360                 365

Gly Val Thr Gly Leu Asn Leu Glu His His His His His His
    370                 375                 380

<210> SEQ ID NO 5
<211> LENGTH: 209
<212> TYPE: PRT
<213> ORGANISM: Artificial Sequence
<220> FEATURE:
<223> OTHER INFORMATION: Description of Artificial Sequence: Synthetic
      BoDV-P (23 kDa, His-Tag)

<400> SEQUENCE: 5

Met Ala Thr Arg Pro Ser Ser Leu Val Asp Ser Leu Glu Asp Glu Glu
1               5                   10                  15

Asp Pro Gln Thr Leu Arg Arg Glu Arg Ser Gly Ser Pro Arg Pro Arg
            20                  25                  30

Lys Ile Pro Arg Asn Ala Leu Thr Gln Pro Val Asp Gln Leu Leu Lys
        35                  40                  45

Asp Leu Arg Lys Asn Pro Ser Met Ile Ser Asp Pro Asp Gln Arg Thr
    50                  55                  60

Gly Arg Glu Gln Leu Ser Asn Asp Glu Leu Ile Lys Lys Leu Val Thr
65                  70                  75                  80

Glu Leu Ala Glu Asn Ser Met Ile Glu Ala Glu Glu Val Arg Gly Thr
                85                  90                  95

Leu Gly Asp Ile Ser Ala Arg Ile Glu Ala Gly Phe Glu Ser Leu Ser
            100                 105                 110

Ala Leu Gln Val Glu Thr Ile Gln Thr Ala Gln Arg Cys Asp His Ser
        115                 120                 125

Asp Ser Ile Arg Ile Leu Gly Glu Asn Ile Lys Ile Leu Asp Arg Ser
    130                 135                 140

Met Lys Thr Met Met Glu Thr Met Lys Leu Met Met Glu Lys Val Asp
145                 150                 155                 160

Leu Leu Tyr Ala Ser Thr Ala Val Gly Thr Ser Ala Pro Met Leu Pro
                165                 170                 175

Ser His Pro Ala Pro Pro Arg Ile Tyr Pro Gln Leu Pro Ser Ala Pro
            180                 185                 190

```
Thr Ala Asp Glu Trp Asp Ile Ile Pro Leu Glu His His His His
        195                 200                 205
His

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic
      VSBV-N peptide, amino acids 116-130 of A0A0H5BWD6

<400> SEQUENCE: 6

Phe Val Lys Val Ser Arg Phe Tyr Gly Glu Arg Thr Ala Ser Arg
1               5                   10                  15

<210> SEQ ID NO 7
<211> LENGTH: 938
<212> TYPE: PRT
<213> ORGANISM: Artificial Sequence
<220> FEATURE:
<223> OTHER INFORMATION: Description of Artificial Sequence: Synthetic
      NR1 NMDAR

<400> SEQUENCE: 7

Met Ser Thr Met His Leu Leu Thr Phe Ala Leu Leu Phe Ser Cys Ser
1               5                   10                  15

Phe Ala Arg Ala Ala Cys Asp Pro Lys Ile Val Asn Ile Gly Ala Val
                20                  25                  30

Leu Ser Thr Arg Lys His Glu Gln Met Phe Arg Glu Ala Val Asn Gln
            35                  40                  45

Ala Asn Lys Arg His Gly Ser Trp Lys Ile Gln Leu Asn Ala Thr Ser
        50                  55                  60

Val Thr His Lys Pro Asn Ala Ile Gln Met Ala Leu Ser Val Cys Glu
65                  70                  75                  80

Asp Leu Ile Ser Ser Gln Val Tyr Ala Ile Leu Val Ser His Pro Pro
                85                  90                  95

Thr Pro Asn Asp His Phe Thr Pro Thr Pro Val Ser Tyr Thr Ala Gly
            100                 105                 110

Phe Tyr Arg Ile Pro Val Leu Gly Leu Thr Thr Arg Met Ser Ile Tyr
        115                 120                 125

Ser Asp Lys Ser Ile His Leu Ser Phe Leu Arg Thr Val Pro Pro Tyr
    130                 135                 140

Ser His Gln Ser Ser Val Trp Phe Glu Met Met Arg Val Tyr Asn Trp
145                 150                 155                 160

Asn His Ile Ile Leu Leu Val Ser Asp Asp His Glu Gly Arg Ala Ala
                165                 170                 175

Gln Lys Arg Leu Glu Thr Leu Leu Glu Glu Arg Glu Ser Lys Ala Glu
            180                 185                 190

Lys Val Leu Gln Phe Asp Pro Gly Thr Lys Asn Val Thr Ala Leu Leu
        195                 200                 205

Met Glu Ala Arg Glu Leu Glu Ala Arg Val Ile Ile Leu Ser Ala Ser
    210                 215                 220

Glu Asp Asp Ala Ala Thr Val Tyr Arg Ala Ala Ala Met Leu Asn Met
225                 230                 235                 240

Thr Gly Ser Gly Tyr Val Trp Leu Val Gly Glu Arg Glu Ile Ser Gly
                245                 250                 255
```

-continued

Asn Ala Leu Arg Tyr Ala Pro Asp Gly Ile Ile Gly Leu Gln Leu Ile
                260                 265                 270

Asn Gly Lys Asn Glu Ser Ala His Ile Ser Asp Ala Val Gly Val Val
            275                 280                 285

Ala Gln Ala Val His Glu Leu Leu Glu Lys Glu Asn Ile Thr Asp Pro
        290                 295                 300

Pro Arg Gly Cys Val Gly Asn Thr Asn Ile Trp Lys Thr Gly Pro Leu
305                 310                 315                 320

Phe Lys Arg Val Leu Met Ser Ser Lys Tyr Ala Asp Gly Val Thr Gly
                325                 330                 335

Arg Val Glu Phe Asn Glu Asp Gly Asp Arg Lys Phe Ala Asn Tyr Ser
            340                 345                 350

Ile Met Asn Leu Gln Asn Arg Lys Leu Val Gln Val Gly Ile Tyr Asn
        355                 360                 365

Gly Thr His Val Ile Pro Asn Asp Arg Lys Ile Ile Trp Pro Gly Gly
    370                 375                 380

Glu Thr Glu Lys Pro Arg Gly Tyr Gln Met Ser Thr Arg Leu Lys Ile
385                 390                 395                 400

Val Thr Ile His Gln Glu Pro Phe Val Tyr Val Lys Pro Thr Met Ser
                405                 410                 415

Asp Gly Thr Cys Lys Glu Glu Phe Thr Val Asn Gly Asp Pro Val Lys
            420                 425                 430

Lys Val Ile Cys Thr Gly Pro Asn Asp Thr Ser Pro Gly Ser Pro Arg
        435                 440                 445

His Thr Val Pro Gln Cys Cys Tyr Gly Phe Cys Ile Asp Leu Leu Ile
    450                 455                 460

Lys Leu Ala Arg Thr Met Asn Phe Thr Tyr Glu Val His Leu Val Ala
465                 470                 475                 480

Asp Gly Lys Phe Gly Thr Gln Glu Arg Val Asn Asn Ser Asn Lys Lys
                485                 490                 495

Glu Trp Asn Gly Met Met Gly Glu Leu Leu Ser Gly Gln Ala Asp Met
            500                 505                 510

Ile Val Ala Pro Leu Thr Ile Asn Asn Glu Arg Ala Gln Tyr Ile Glu
        515                 520                 525

Phe Ser Lys Pro Phe Lys Tyr Gln Gly Leu Thr Ile Leu Val Lys Lys
530                 535                 540

Glu Ile Pro Arg Ser Thr Leu Asp Ser Phe Met Gln Pro Phe Gln Ser
545                 550                 555                 560

Thr Leu Trp Leu Leu Val Gly Leu Ser Val His Val Val Ala Val Met
                565                 570                 575

Leu Tyr Leu Leu Asp Arg Phe Ser Pro Phe Gly Arg Phe Lys Val Asn
            580                 585                 590

Ser Glu Glu Glu Glu Asp Ala Leu Thr Leu Ser Ser Ala Met Trp
        595                 600                 605

Phe Ser Trp Gly Val Leu Leu Asn Ser Gly Ile Gly Glu Gly Ala Pro
610                 615                 620

Arg Ser Phe Ser Ala Arg Ile Leu Gly Met Val Trp Ala Gly Phe Ala
625                 630                 635                 640

Met Ile Ile Val Ala Ser Tyr Thr Ala Asn Leu Ala Ala Phe Leu Val
                645                 650                 655

Leu Asp Arg Pro Glu Glu Arg Ile Thr Gly Ile Asn Asp Pro Arg Leu
            660                 665                 670

```
Arg Asn Pro Ser Asp Lys Phe Ile Tyr Ala Thr Val Lys Gln Ser Ser
        675                 680                 685

Val Asp Ile Tyr Phe Arg Arg Gln Val Glu Leu Ser Thr Met Tyr Arg
    690                 695                 700

His Met Glu Lys His Asn Tyr Glu Ser Ala Ala Glu Ala Ile Gln Ala
705                 710                 715                 720

Val Arg Asp Asn Lys Leu His Ala Phe Ile Trp Asp Ser Ala Val Leu
                725                 730                 735

Glu Phe Glu Ala Ser Gln Lys Cys Asp Leu Val Thr Thr Gly Glu Leu
            740                 745                 750

Phe Phe Arg Ser Gly Phe Gly Ile Gly Met Arg Lys Asp Ser Pro Trp
        755                 760                 765

Lys Gln Asn Val Ser Leu Ser Ile Leu Lys Ser His Glu Asn Gly Phe
    770                 775                 780

Met Glu Asp Leu Asp Lys Thr Trp Val Arg Tyr Gln Glu Cys Asp Ser
785                 790                 795                 800

Arg Ser Asn Ala Pro Ala Thr Leu Thr Phe Glu Asn Met Ala Gly Val
                805                 810                 815

Phe Met Leu Val Ala Gly Gly Ile Val Ala Gly Ile Phe Leu Ile Phe
            820                 825                 830

Ile Glu Ile Ala Tyr Lys Arg His Lys Asp Ala Arg Arg Lys Gln Met
            835                 840                 845

Gln Leu Ala Phe Ala Ala Val Asn Val Trp Arg Lys Asn Leu Gln Asp
        850                 855                 860

Arg Lys Ser Gly Arg Ala Glu Pro Asp Pro Lys Lys Lys Ala Thr Phe
865                 870                 875                 880

Arg Ala Ile Thr Ser Thr Leu Ala Ser Ser Phe Lys Arg Arg Arg Ser
            885                 890                 895

Ser Lys Asp Thr Ser Thr Gly Gly Gly Arg Gly Ala Leu Gln Asn Gln
            900                 905                 910

Lys Asp Thr Val Leu Pro Arg Arg Ala Ile Glu Arg Glu Glu Gly Gln
        915                 920                 925

Leu Gln Leu Cys Ser Arg His Arg Glu Ser
930                 935
```

METHOD FOR THE DIAGNOSIS OF BORNAVIRUS INFECTION

CROSS-REFERENCE TO RELATED APPLICATIONS

The present application claims priority to European patent application EP 17 211 138.7 filed Dec. 29, 2017, the content of which is incorporated by reference in its entirety.

REFERENCE TO A SEQUENCE LISTING

The instant application contains a Sequence Listing which has been filed electronically in ASCII format and is hereby incorporated by reference in its entirety. Said ASCII copy, created on Dec. 17, 2018, is named 000712US_SL.txt and is 21,768 bytes in size.

BACKGROUND OF THE INVENTION

Field of the Invention

The present invention relates to a method for diagnosing a limbic encephalitis, paraneoplastic syndrome (PNS), encephaloymyelitis, leukoencephalopathy, retinitis or optic atrophy, comprising the step of detecting a bornavirus in a sample, preferably from the group comprising mammalian 2 bornavirus, even more preferably VSBV-1, and mammalian 1 bornavirus, even more preferably BoDV-1; to a carrier comprising a means for the capture of an antibody against at least one polypeptide selected from the group comprising BoDV-1-N, BoDV-1-P, VSBV-N and VSBV-P; to a kit comprising the carrier according to the invention and also a means for the detection of a captured antibody and a control for the detection of the presence of a sample; and to the use of a carrier or kit or of a primer suitable for the detection of a bornavirus or of just such a probe for the diagnosis of an encephalitis, for the prognostication of post-transplantation complications, for the monitoring of a therapy of an encephalitis or of post-transplantation complications or for the differentiation between an autoimmune encephalitis and an encephalitis caused by infection.

Description of Related Art

An encephalitis is an inflammation of the brain that is caused by an infection, a paraneoplastic disease or by an autoimmune disease. The patients suffer from a multiplicity of non-specific symptoms such as fever, headaches, paralyses, visual disturbances, cramps, loss of consciousness, and perception and orientation disorders.

With timely identification, there are treatment approaches which are effective for many encephalitises, but which differ considerably depending on the cause of the disease. Whereas a brain inflammation caused by bacteria can be treated with antibiotics and a viral encephalitis can be treated by intravenous administration of antiviral agents such as acyclovir, what is indicated in the case of an encephalitis caused by autoimmunity is the administration of immunosuppressive agents.

In many cases, an encephalitis is not noticed at all in the case of mild manifestation. The earlier the treatment of the disease, the better, and it is therefore of particular importance to be able to make the diagnosis at an early stage and in a reliable manner despite the non-specific and possibly mild symptoms. Incorrectly treated or untreated, it can lead to a severe disease with lasting damage such as paralyses, speech disorders and mental disability. In the case of bacterial encephalitises, the mortality rate is up to 50 percent; in the case of an encephalitis caused by Herpes simplex, it is even 70 percent.

Recent years have seen the discovery of a multiplicity of manifestations of viral or autoimmunity-caused encephalitises, for example encephalitises caused by autoantibodies against NMDAR (EP2057466 B1), GABA(A) (EP2863231 A1), GABA(B) (EP2483417 B1), DPPX (U.S. Pat. No. 9,719,993 BB), Lgl1 (U.S. Pat. No. 9,250,250 BB), IGLON5 (EP2905622 A1), SNARE (EP17001205), NBC1 (EP3026434 A1), flotillin (EP3101424 A1) and ITPR (EP3018478 A1).

Nevertheless, there is still a large number of patients who suffer from a disease with symptoms typical of encephalitis, but cannot be diagnosed correctly (Bloch and Glaser (2007) Diagnostic approaches for patients with suspected encephalitis. Current Infectious Disease Reports (4):315-22). This concerns especially the group of patients with a limbic encephalitis, which is described in the literature as being caused by autoimmunity without exception (Melzer et al. (2015) Limbic Encephalitis: Potential Impact of Adaptive Autoimmune Inflammation on Neuronal Circuits of the Amygdala. Front. Neurol. 3; 6:171).

A particularly vulnerable group are patients who undergo an organ transplantation. Apart from the anyway weakened state of said patients, the administration over many years of medicaments, immunosuppressants in high doses after the transplantation, promotes the outbreak of a very wide variety of diseases such as opportunistic infections. A significant problem especially when transplanting solid organs are neurological complications, which at any rate affect from 10% to 59% of recipients (Senzolo et al. (2009) Neurologic complications after solid organ transplantation. Transpl. Int. (3):269-78, 10-59%).

In many cases, it is unclear what these neurological complications are caused by. Possibilities include not only neurological infection symptoms, but also the neurotoxicity of the administered immunosuppressants. For instance, the administration of corticosteroids leads to an elevated risk of a myopathy. Liver failure, too, may be manifested in the form of neurological symptoms (Shalimar et al. (2015) Management in Acute Liver Failure. J. Clin. Exp. Hepatol. (5):S104-S115).

Bornavirus infections in mammals were already described more than 100 years ago. In the case of horses, the mammalian bornavirus BoDV-1 is known to cause encephalitis. What occurs in this case is a persistent disease in the central nervous system, as a consequence of which there is development of a non-purulent meningoencephalitis (inflammation of brain and cerebral membrane). Sick animals develop motor disorders, are distinguished by behavioural problems and, in many cases, die as a result of the infection.

Hoffmann et al. (2015) A variegated squirrel bornavirus associated with fatal human encephalitis, N Engl J Med 2015; 373, pages 154-162, describe a terminal virus infection of a plurality of older male patients having pre-existing conditions (high blood pressure, diabetes and/or obesity) with a bornavirus which affects variegated squirrels ("VSBV-1", i.e. Variegated Squirrel Bornavirus-1). All the patients suffered from a thrombosis, which led to pulmonary embolism. The patients suffered from encephalitis, which however was not a limbic encephalitis, but a syndrome with oedematous lesions in the cerebral cortical regions without limbic distribution. An indirect immunofluorescence test (IIFT) based on a feline cell line infected with the complete BoDV-1 virus was used to detect antibodies against bornaviruses.

At the beginning of the 2000s, a working group reported on a supposed link between psychiatric disorders and an infection with bornaviruses of the species which affects horses. These results could not be reproduced by independent experts and are therefore not acknowledged in professional circles. On the contrary, the Robert Koch Institute comes to the conclusion: "According to the present findings, the test described by Bode et al. (2001) must be considered to be unsuitable for meaningful diagnostics." (https://www.rki.de/DE/Content/Forsch/Forschungsschwerpunkte/NeueRisiken/NeuartigeErrege r/Einstellung_Projekt_Bornavirus.html, retrieved on 14 Dec. 2017). An encephalitis caused by BoDV-1 in humans has hitherto not been described in the prior art.

In a press statement, the Friedrich Löffler Institute reports on the development of a test for the detection of VSBV-1 (http://www.wir-sind-tierarzt.de/2015/07/bestaetigt-bunthoemchen-uebertragen-bornaviren/, retrieved on 14 Dec. 2017).

BRIEF SUMMARY OF THE INVENTION

Against this background, it is the object of the present invention to provide an improved detection system for the diagnosis of a viral infection, more particularly a bornaviral infection, preferably with improved diagnostic reliability, particularly with respect to specificity and/or sensitivity, relative to the systems described in the prior art.

Furthermore, it is the object of the invention to provide a detection system for the diagnosis, more particularly differential diagnosis, of encephalitis, focussing on limbic encephalitis, that makes it possible in particular to distinguish between an autoimmune encephalitis and an encephalitis caused by infection, particularly one caused by a viral infection, even more preferably by a limbic encephalitis.

Furthermore, it is the object of the invention to provide a detection system which makes it possible to diagnose, treat and prevent post-transplantation complications, particularly complications with neurological symptoms.

The object of the invention is achieved by the subject matter described below.

Embodiments of the present invention include:
1. Method for diagnosing a limbic encephalitis, PNS, encephaloymyelitis, leukoencephalopathy, retinitis or optic atrophy, comprising the step of detecting a bornavirus, preferably from the group comprising mammalian 2 bornavirus, even more preferably VSBV-1, and mammalian 1 bornavirus, even more preferably BoDV-1, in a sample, preferably a human sample.
2. Method for prognosticating neurological post-transplantation complications or for screening organ donors or donor organs, comprising the step of detecting a bornavirus in a sample, preferably a human sample.
3. Method for differentiating between an autoimmune encephalitis and an encephalitis caused by infection, comprising the step of detecting a bornavirus in a sample, preferably a human sample.
4. Method according to any of 1 to 3, wherein the detection is achieved by detecting an antibody against a bornavirus-specific polypeptide in the sample, preferably from the group comprising an N, P and X protein of the bornavirus.
5. Method according to 4, wherein the sample is contacted with a carrier comprising a means for the capture of an antibody against at least one polypeptide selected from the group comprising BoDV-1-N, BoDV-1-P, BoDV-1-X, VSBV-N, VSBV-P and VSBV-X.
6. Method according to 5, wherein a captured antibody is detected by means of enzyme activity, fluorescence or chemiluminescence.
7. Method according to any of 1 to 6, wherein the carrier is selected from the group comprising a membrane-based immunoblot, preferably a Western blot or a line blot, one or more than one bead, a biochip arranged for immunofluorescence, and an ELISA microtiter plate.
8. Carrier comprising a means for the capture of an antibody against at least one polypeptide selected from the group comprising BoDV-1-N, BoDV-1-P, BoDV-1-X, VSBV-N, VSBV-P and VSBV-X.
9. Method or carrier according to any of 5 to 8, wherein the carrier further comprises a means for the capture of an antibody against at least one virus from the group comprising herpes simplex HSV-1, herpes simplex HSV-2, human herpesvirus HHV-6, human herpesvirus HHV-7, rabies virus, LCMV, West Nile virus, tick-borne encephalitis virus, Usutu virus, Toscana virus, varicella zoster virus, Epstein-Barr virus, cytomegalovirus, equine encephalitis viruses, chikungunya virus, La Crosse virus, Rift Valley fever virus, St. Louis encephalitis virus, influenza A virus, measles virus, mumps virus, rubella virus, Hendra virus, Nipah virus, enterovirus, California encephalitis virus, Powassan virus, Murray Valley encephalitis virus and Japanese encephalitis virus.
10. Method or carrier according to any of 5 to 9, wherein the carrier further comprises a means for the capture of an antibody against a neurological antigen from the group comprising NMDAR, AMPAR, GAD65, amphiphysin, GABA(A), GABA(B), DPPX, Lgl1, CASPR2, IGLON5, SNARE, NBC1, flotillin and ITPR, preferably NMDAR.
11. Kit comprising the carrier according to any of 8 to 10 and also a means for the detection of a captured antibody or a control for the detection of the presence of a sample, preferably a serum or CSF sample.
12. Use of the carrier or kit according to any of 8 to 11 or of a primer suitable for the detection of a bornavirus or of just such a probe for the diagnosis of an encephalitis, PNS, encephaloymyelitis, leukoencephalopathy, retinitis or optic atrophy, for the prognostication of post-transplantation complications, for the monitoring of a therapy of an encephalitis or of post-transplantation complications or for the differentiation between an autoimmune encephalitis and an encephalitis caused by infection.
13. Use of a carrier or kit according to any of 8 to 11 or of a carrier comprising a means for the capture of an antibody against NMDAR for the differentiation between an autoimmune encephalitis and an encephalitis caused by infection, preferably a limbic encephalitis.
14. Use of an antigenic polypeptide from the group comprising BoDV-1-N, BoDV-1-P, VSBV-N, VSBV-P, NMDAR, AMPAR, GAD65, amphiphysin, GABA(A), GABA(B), DPPX, Lgl1, CASPR2, IGLON5, SNARE, NBC1, flotillin and ITPR or a variant thereof for the preparation of a diagnostic or a kit for the diagnosis of encephalitis, preferably differential diagnosis of limbic encephalitis.
15. Use of a medicament effective against bornaviruses for the prevention or treatment of post-transplantation complications or of encephalitis, preferably limbic encephalitis, PNS, encephaloymyelitis, leukoencephalopathy, retinitis or optic atrophy.

BRIEF DESCRIPTION OF THE SEVERAL VIEWS OF THE DRAWING

FIG. 1 shows the structure of a line blot strip with bornaviral antigens, as prepared and used in Example 1.

FIG. 4 shows the results of the testing of samples from patients with limbic encephalitis using a further line blot strip prepared in Example 1.

FIG. 6 shows the testing of samples from a transplantation patient using a line blot strip with bornaviral antigens that was prepared as per Example 1; see Example 2.

DETAILED DESCRIPTION OF THE INVENTION

Figure 2:
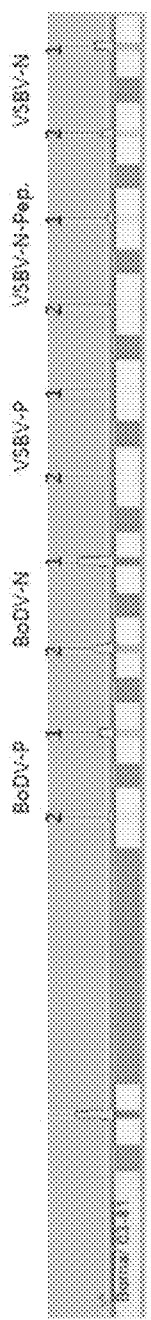
FIG. 2 shows a line blot strip with bornaviral antigens, as prepared in Example 1, after the incubation as per Example 1.

In a first aspect, the object of the invention is achieved by a method for diagnosing a limbic encephalitis, PNS, encephaloymyelitis, leukoencephalopathy, retinitis or optic atrophy, comprising the step of detecting a bornavirus, preferably from the group comprising mammalian 2 bornavirus, even more preferably VSBV-1, and mammalian 1 bornavirus, even more preferably BoDV-1, in a sample, preferably a human sample.

In a second aspect, the object of the invention is achieved by a method for prognosticating neurological post-transplantation complications or for screening organ donors or donor organs, comprising the step of detecting a bornavirus in a sample, preferably a human sample.

In a third aspect, the object of the invention is achieved by a method for differentiating between an autoimmune encephalitis and an encephalitis caused by infection, comprising the step of detecting a bornavirus in a sample, preferably a human sample.

In a preferred embodiment, the detection is achieved by detecting an antibody against a bornavirus-specific polypeptide in the sample, preferably from the group comprising an N, P and X protein of the bornavirus.

In a further preferred embodiment, the sample is contacted with a carrier comprising a means for the capture of an antibody against at least one polypeptide selected from the group comprising BoDV-1-N, BoDV-1-P, BoDV-1-X, VSBV-N, VSBV-P and VSBV-X.

In a further preferred embodiment, a captured antibody is detected by means of enzyme activity, fluorescence or chemiluminescence.

In a further preferred embodiment, the carrier is selected from the group comprising a membrane-based immunoblot, preferably a Western blot or a line blot, one or more than one bead, a biochip arranged for immunofluorescence, and an ELISA microtiter plate.

In a fourth aspect, the object of the invention is achieved by a carrier comprising a means for the capture of an antibody against at least one polypeptide selected from the group comprising BoDV-1-N, BoDV-1-P, BoDV-1-X, VSBV-N, VSBV-P and VSBV-X.

In a preferred embodiment, the carrier further comprises a means for the capture of an antibody against at least one virus from the group comprising herpes simplex HSV-1, herpes simplex HSV-2, human herpesvirus HHV-6, human herpesvirus HHV-7, rabies virus, LCMV, West Nile virus, tick-borne encephalitis virus, Usutu virus, Toscana virus, varicella zoster virus, Epstein-Barr virus, cytomegalovirus, equine encephalitis viruses, chikungunya virus, La Crosse virus, Rift Valley fever virus, St. Louis encephalitis virus, influenza A virus, measles virus, mumps virus, rubella virus, Hendra virus, Nipah virus, enterovirus, California encephalitis virus, Powassan virus, Murray Valley encephalitis virus and Japanese encephalitis virus.

In a preferred embodiment, the carrier further comprises a means for the capture of an antibody against a neurological antigen from the group comprising NMDAR, AMPAR, GAD65, amphiphysin, GABA(A), GABA(B), DPPX, Lgl1, CASPR2, IGLON5, SNARE, NBC1, flotillin and ITPR.

In a fifth aspect, the object of the invention is achieved by a kit comprising the carrier according to the invention and also a means for the detection of a captured antibody or a control for the detection of the presence of a sample.

In a sixth aspect, the object of the invention is achieved by the use of the carrier or kit according to the invention or of a primer suitable for the detection of a bornavirus or of just such a probe or of a means for the detection of an antibody against a bornavirus for the diagnosis of an encephalitis, PNS, encephaloymyelitis, leukoencephalopathy, retinitis or optic atrophy, for the prognostication of post-transplantation complications, for the monitoring of a therapy of an encephalitis or of post-transplantation complications or for the differentiation between an autoimmune encephalitis and an encephalitis caused by infection.

In a seventh aspect, the object of the invention is achieved by the use of a carrier or kit according to the invention or of a carrier comprising a means for the capture of an antibody against NMDAR for the differentiation between an autoimmune encephalitis and an encephalitis caused by infection, preferably a limbic encephalitis.

In an eighth aspect, the object of the invention is achieved by the use of an antigenic polypeptide from the group comprising BoDV-1-N, BoDV-1-P, VSBV-N, VSBV-P, NMDAR, AMPAR, GAD65, amphiphysin, GABA(A), GABA(B), DPPX, Lgl1, CASPR2, IGLON5, SNARE, NBC1, flotillin and ITPR or a variant thereof for the preparation of a diagnostic or a kit for the diagnosis of encephalitis, preferably differential diagnosis of limbic encephalitis.

In a ninth aspect, the object of the invention is achieved by the use of a medicament effective against bornaviruses for the prevention or treatment of post-transplantation complications or of encephalitis, preferably limbic encephalitis.

The present invention is based on the surprising finding from the inventors that an infection with bornaviruses in patients, particularly human patients, can be diagnosed particularly reliably when a relevant sample is tested for antibodies not only against a species of bornavirus, but also for antibodies against BoDV-1 and VSBV.

Furthermore, the present invention is based on the surprising finding from the inventors that a limbic encephalitis can occur not only in the form of an autoimmune disease, but also as the result of a viral infection, particularly an infection with bornaviruses, and that it can be diagnosed by detection of an antibody against a bornavirus.

Furthermore, the present invention is based on the surprising finding from the inventors that post-transplantation complications comprising neurological symptoms and diseases, respectively encephaloymyelitis, leukoencephalopathy, retinitis or optic atrophy, can be caused by the transmission of bornavirus, particularly BoDV-1, and can be diagnosed and appropriately treated via the detection of antibodies against bornaviruses. Furthermore, it is possible to check the quality of organ donors and donor organs by detecting in samples thereof antibodies against a bornavirus. Similarly, it is possible to clarify whether a prophylactic antiviral treatment or immunization of an organ recipient is indicated.

In a preferred embodiment, the term "limbic encephalitis", as used herein, is understood to mean a neurological disease of the central nervous system, in which an MRI examination shows an abnormal signal intensity in the brain areas belonging to the limbic system, particularly temporomedial signal rises, more particularly those which do not normalize within a few days. Even more preferably, at least one of the three symptoms from the group consisting of short-term memory disorder, temporal lobe seizures and affect disorder occurs. Characteristic MRI recordings are disclosed in the literature, for example in Simnon/Greenberg/Aminoff, Clinical Neurology, 7th edition. 2009 at FIG. 1-23.

In a preferred embodiment, the term "diagnose", as used herein, is understood to mean a procedure in which information is obtained that assists the assessment, or allows the assessment in the first place, as to whether a subject is suffering from a disease or is suffering from a disease with a higher probability than an average person or suffered in the past or will suffer in the future, and also as to whether a disease is progressing or how it will develop in the future, or in order to assess whether a certain treatment is working. For example, the detection of a bornavirus in a sample from a donor or a donor organ shows that the probability of post-transplantation complications caused by a bornavirus is increased. Furthermore, such a detection shows that a patient can benefit from an antiviral treatment, for example with ribavirin, but not from an immunosuppressive treatment, which is aimed at preventing or reducing the formation of autoantibodies. In other words, the term "diagnose" encompasses not only making a diagnosis, but also prognostication and monitoring of the progress of a disease or of the success of therapy in the case of a disease.

Preferably, it is sufficient for the diagnosis to merely detect whether the antibody is present, it being possible to determine whether detectable concentrations of the antibody are present in the sample. In a preferred embodiment, what is determined is whether the relative concentration of the antibody in a patient to be diagnosed is higher than in an average healthy person. What can be determined is whether the concentration is higher by a factor of 1.1, more preferably 1.2, 1.5, 2, 5, 10, 20, 25, 50, 100, 200, 500, 1000, 10000 or 100000, than in a sample from an average healthy person.

If an antibody against a bornavirus, preferably from the group comprising VSBV-1 or BoDV-1, can be detected, this indicates an increased probability that the patient is suffering from a bornavirus infection or indicates that an encephalitis, preferably limbic encephalitis, is caused by a viral infection, not by an autoimmune disease. Furthermore, the detection of such an antibody in a patient suffering from encephalitis indicates that said patient is not suffering from a PNS and thus from a PNS-associated cancer, for example a small-cell cancer of the lungs.

The detection of an antibody against a bornavirus, and the infection with a bornavirus to be inferred therefrom, argues for a therapeutic or precautionary treatment with an antiviral medicament or respective therapeutic actions. For example, it has been possible to show that ribavirin is effective against bornaviruses. On the other hand, the administration of immunosuppressants would be completely failing, since these are not only associated with significant side effects, but weaken the immune system of the patient against viral and opportunistic infections. The absence of an antibody against a bornavirus and/or the presence of an autoantibody, preferably against NMDAR, argues for a therapeutic or precautionary treatment with an immunosuppressant, for example from the group comprising rituximab, prednisolone, methylprednisolone, cyclophosphamide, mycophenolate mofetil, intravenous immunoglobulins, tacrolimus, ciclosporin, methotrexate and azathioprine.

In a preferred embodiment, what is differentiated is whether the patient to be diagnosed has one or more than one, preferably two or more or three or more different antibodies against a bornavirus, the antibodies being optionally selected from the group of antibodies against BoDV-1-N, BoDV-1-P, BoDV-1-X, VSBV-N, VSBV-P and VSBV-X, more preferably BoDV-1-N, BoDV-1-P, VSBV-N and VSBV-P. More particularly, the detection of an antibody against an antigen from said group can indicate that the patient is suffering from an early or latent infection, whereas the detection of antibodies against more than one antigen, preferably two, three or four antigens, from said group indicates a clinically apparent infection.

A person skilled in the art understands that such a detection generally does not allow a comprehensive diagnosis on its own, but that further aspects must be considered, for example further parameters to be determined in a sample, medical history, clinical symptoms, anamnesis or the results from imaging methods, for example MRI. Said person further understands that the value of the method according to the invention can consist in it being possible to carry out an indirect diagnosis or differential diagnosis in which the ruling out of a disease indicates that the patient is suffering from another disease with similar symptoms. In a preferred embodiment, the detection of an antibody against a bornavirus can indicate that the patient is suffering from a limbic encephalitis which is not an autoimmune disease. Furthermore, such a detection can indicate that the patient is not suffering from a paraneoplastic syndrome and/or a cancer, preferably a small-cell lung cancer. Conversely, the detection of an autoantibody against the NMDA receptor can indicate that the patient is not suffering from a virally caused encephalitis, particularly limbic encephalitis.

In a preferred embodiment, a person skilled in the art attaches importance to clinical symptoms mentioned herein, as is apparent from relevant textbooks on the priority date, for example Simon/Greenberg/Aminoff, Clinical Neurology, 7th edition, 2009.

The bornavirus is preferably a bornavirus which affects mammals. Even more preferably, the bornavirus is a bornavirus which affects humans. In a particularly preferred embodiment, the bornavirus is selected from the group comprising mammalian 2 bornavirus, even more preferably VSBV-1, and mammalian 1 bornavirus, even more preferably BoDV-1.

In a preferred embodiment, "mammalian 1 bornavirus", as used herein, encompasses AJ311524_BoDV-2_1998, AJ311522_BoDV-1_1980, BDU04608_BoDV-1_1929, AJ311523_BoDV-1_1994, AB246670_BoDV-1_2004, and AB258389_BoDV-1_1997, cf. Tappe et al. (2018) Fatal limbic encephalitis in a zoo animal caretaker caused by variegated squirrel bornavirus: Zoonotic bornaviruses as occupational risk, manuscript submitted.

In a preferred embodiment, "mammalian 2 bornavirus", as used herein, encompasses LT594387_BH122/15-2_*C. prevostii*_2015, KY488724_BH22/16-36_*C. prevostii*_2016, KY488723_BH22/16-37_*C. prevostii*_2016, KY488727_BH22/16-16_*T. swinhoei*_2016, LT594389_BH49/15-1_*C. prevostii*_2015, KY488726_BH22/16-34_*C. prevostii*_2016, LT594388_BH133/15_*C. prevostii*_2015, KY488722_BH22/16-38_*C. prevostii*_2016, KY488725_BH22/16-35_*C. finlaysonii*_2016, LT594383_BH3/16-2_*C. prevostii*_2016, LT594381_BH122/15-1_*C. prevostii*_2015, LT594382_BH48/15-1_*S. variegatoides*_2015, LN713681_*H. sapiens* 2015, LN713680_*S. variegatoides*_2015, LT594386_BH3/16-1_*C. prevosi*_2016, LT594384_BH49/15-6_*S. variegatoides*_2015, LT594385_BH49/15-11_*S. variegatoides*_2015, LT594391_BH48/15-2_*S. variegatoides*_2015, LT594390_BH75/15_*S. variegatoides*_2015, KY488728_BH21/16_*C. prevostii*_2016, MF597762_BH55/16_*H. sapiens*_2016 and KY488729_BH12/16_*C. prevostii*_2016, cf. Tappe et al. (2018) Fatal limbic encephalitis in a zoo animal caretaker caused by variegated squirrel bornavirus: Zoonotic bornaviruses as occupational risk, manuscript submitted.

All bornaviruses can be identified by whole genome sequencing using the methodology as described in Shahhosseini N, Lühken R, Jöst H, Jansen S, Börstler J, Rieger T, Krüger A, Yadouleton A, de Mendonga Campos R, Cime-Santos C C, Ferreira D F, Garms R, Becker N, Tannich E, Cadar D, Schmidt-Chanasit J. (2017) Infect Genet Evol.; 55:260-268, in combination with the data published by Tappe et al. (2018) Fatal limbic encephalitis in a zoo animal caretaker caused by variegated squirrel bornavirus: Zoonotic bornaviruses as occupational risk, manuscript submitted.

The sample to be tested is, if antibodies are being detected, a sample containing a representative set of antibodies from the patient. Preferably, it is selected from the group comprising serum, plasma, saliva and CSF.

In a particularly preferred embodiment, the virus is also identified and detected by molecular genetic means using bornavirus-specific primers and probes, preferably via PCR, even more preferably reverse transcription PCR. The primer and/or probes can be specific for BoDV-1 and/or for VSBV-1. Exemplary primers, probes and a corresponding protocol for the detection of VSBV-1 are described in Hoffmann et al. (2015) A variegated squirrel bornavirus associated with fatal human encephalitis, N Engl J Med 2015; 373, pages 154-162. Appropriate reagents and methods for a broad-spectrum test for the detection of all known mammalian bornaviruses and of the majority of bornaviruses affecting birds as well as reagents and methods for the detection of BoDV-1 are described in Bourg et al. (2016) Virology Journal; 13:151.

In short, a bornavirus can be detected in a human sample by molecular genetic means by first extracting viral nucleic acids from the sample using commercially available kits [MagMAX™ Viral RNA Isolation Kit (Life Technologies, Carlsbad, Calif., USA)]. Thereafter, the virus genome can be determined by sequencing [Schlottau et al., 2018] and comparison of the obtained sequence with known sequences from the literature, for example [Schlottau et al., 2018; GenBank: LN713681 for VSBV-1; KU748787, AJ311521, AY374521, AY374519, for BoDV-1; AJ311524 for BoDV-2].

Alternatively, a bornavirus can be detected by means of RT-PCR. To this end, viral RNA can be extracted using suitable kits such as the Viral Mini Kit (Qiagen). The detection of a bornavirus can be achieved by amplification of a 61 bp fragment of the P gene and of the end of the X gene using the primers "forward primer Borna-2048-F": 5'-CGC GAC CMT CGA GYC TRG T-3' and "reverse primer Borna-2118-R": 5'-GAC ARC TGY TCC CTT CCK GT-3' that are described in Bourg et al. (2016). The detection is achieved by means of agarose gel electrophoresis. A quantitative detection of BODV-1 can be achieved by amplification of a 161 bp fragment of the X and P gene using the following primers and probe: BoDV1-1288-F TAGTYAGGAGGCTCAATGGCA, BoDV-1449-R GTCCYTCAGGAGCTGGTC, BoDV1-1346-probe FAM-AAGAAGATCCCCAGACACTACGACG-BHQ1 (Schlottau et al., 2018). A quantitative detection of BODV-1 can be achieved by amplification of a 74 bp fragment of the M and G gene using the following primers and probe: BoDV1-2262-F CAATYAATGCAGCYTTCAATGTCTT, BoDV1-2336-R GAATGTCYGGGCCGAGAG, BoDV-2316-probe FAM-CCARCACCAATGTTCCGAAGCCG-BHQ1 (Schlottau et al., 2018).

The virus can also be detected by immunohistochemical means by examination of tissue sections. This is an option when examining donor organs, for which there are no blood samples.

In a preferred embodiment, the term "post-transplantation complications", as used herein, is understood to mean complications after transplantation of a body part, preferably of a tissue or solid organ, even more preferably of a solid organ which is even more preferably selected from the group comprising liver, kidney, lung, intestine, pancreas and heart. In a particularly preferred embodiment, the complications encompass the occurrence of neurological symptoms and can encompass an encephalitis, preferably limbic encephalitis. In a further particularly preferred embodiment, infections occur in the case of "post-transplantation complications". In a preferred embodiment, a neurological symptom is selected from the group comprising tetraplegia, neuropathy, clouding of consciousness, dysarthria, bradykinesia, tremor, unsteady gait, impaired cognitive skills and memory and neuritis. In a particularly preferred embodiment, the post-transplantation complications encompass an impairment of visual function, preferably neurological ophthalmological symptoms and/or diseases, particularly preferably an optic atrophy.

In terms of time, "post-transplantation complications" are preferably complications which occur after the surgical procedure on the recipient, preferably up to one month, in the first six months or later than six months after the procedure.

For the screening of organ donors or donor organs, a suitable sample can be collected from the donors or their organs before the transplantation is carried out. In the case of donors, preference is given to a blood, saliva or CSF sample. In the case of organs, what are tested are blood or tissue residues, respectively samples. The tissue can originate from an organ selected from the group comprising liver, kidney, lung, intestine, pancreas, heart and brain.

In a preferred embodiment, an "autoimmune encephalitis", as used herein, is understood to mean an encephalitis associated with the occurrence of one or more than one autoantibody. The autoantibody is preferably an autoantibody against a neuronal autoantigen, preferably selected from the group comprising NMDAR (EP2057466 B1), GABA(A) (EP2863231 A1), GABA(B) (EP2483417 B1), DPPX (U.S. Pat. No. 9,719,993 BB), Lgl1 or CASPR2 (U.S. Pat. No. 9,250,250 BB), IGLON5 (EP2905622 A1), SNARE (EP17001205), NBC1 (EP3026434 A1), flotillin (EP3101424 A1), DAGLA (EP18196867), SNARE (EP17001205) and ITPR (EP3018478 A1). Appropriate sequences of autoantigens are disclosed in the patent specifications indicated between parentheses.

In a preferred embodiment, a bornavirus is detected in a sample. This means that the virus or a molecule derived therefrom or a patient antibody against the virus or the molecule derived therefrom is detected in the sample.

Autoimmunity-caused encephalitis, more particularly NMDA receptor encephalitis, but not an encephalitis caused by infection with a bornavirus, is frequently associated with the occurrence of tumours. In a preferred embodiment, the term "PNS" (paraneoplastic neurological syndrome), as used herein, is understood to mean a systemic disease which is indirectly caused by the presence of a tumour, for example by the tumour producing epitopes or releasing substances such as hormones or releasing them in an elevated quantity, which the cell from which the tumour is derived would not release or would not release in such quantities under comparable circumstances. The direct or indirect consequence may be the formation of autoantibodies which are preferentially directed against structures or parts of the nervous system, and which are in any case directly or indirectly associated with the occurrence of neurological symptoms and preferentially cause them. It is known that NMDA receptor encephalitis may be associated with the occurrence of teratomas of the ovaries. The tumour may be undetectable in the case of an autoimmunity-caused encephalitis.

The detection according to the invention can be achieved via the detection of a polypeptide specific for the bornavirus or of an antibody thereagainst, preferably an antibody thereagainst. The antibody is preferably an antibody against a viral polypeptide from the group comprising BoDV-1-N, BoDV-1-P, BoDV-1-X, VSBV-N, VSBV-P and VSBV-X, preferably BoDV-1-N, BoDV-1-P, VSBV-N and VSBV-P. In a particularly preferred embodiment, what is detected is whether the patient has one, two, three, four or more than one, two, three, four, five or six antibodies against a viral polypeptide from the group comprising BoDV-1-N, BoDV-1-P, BoDV-1-X, VSBV-N, VSBV-P and VSBV-X.

In a preferred embodiment, the carrier comprises, as capture means, an approx. 40 kDa nucleoprotein of a bornavirus. In a preferred embodiment, the carrier comprises, as capture means, an approx. 23 kDa phosphoprotein of a bornavirus. In a preferred embodiment, the carrier comprises, as capture means, one or more than one, two, three, four, five or six polypeptides from the group comprising BoDV-1-N, BoDV-1-P, BoDV-1-X, VSBV-N, VSBV-P and VSBV-X, preferably BoDV-1-N, BoDV-1-P, VSBV-N and VSBV-P, or variants thereof. In a preferred embodiment, the carrier comprises BoDV-1-N and BoDV-1-P or variants thereof. In a preferred embodiment, the carrier comprises VSBV-N and VSBV-P or variants thereof. In a preferred embodiment, the carrier comprises BoDV-1-P and VSBV-P or variants thereof. In a preferred embodiment, the carrier comprises VSBV-N and BoDV-1-N or variants thereof.

In a preferred embodiment, "BoDV-1-N", "BoDV-1-P", "VSBV-N" and "VSBV-P" are understood to mean the sequences described by the Uniprot entries POC796 (BoDV-1-N), POC798 (BoDV-1-P), A0A0H5BWD6 (VSBV-N) and A0A0H5BWK0 (VSBV-P), respectively, on the priority date of the present patent application. VSBV-X preferably has the sequence ART67059.1, and BoDV-1-X preferably has the sequence AIK27011.1. For all items, the version of the database that was available on the priority date and the state of the data that was retrievable on said date is relevant. In a preferred embodiment, an N, P or X protein of a bornavirus is understood to mean a protein having at least 60, 70, 80, 85, 90, 95, 98 or 99% sequence identity in relation to the sequences POC796, POC798 or AIK27011.1, particularly preferably a variant thereof.

In a preferred embodiment, the carrier used according to the invention is a medical device, preferably diagnostic device, which contains a means for the capture of one or more than one antibody. The term "means for the capture of an antibody", as used herein, is understood to mean an agent which binds specifically to an antibody to be detected such that said antibody, alone or in a sufficient quantity, binds more strongly than another antibody, particularly in the form of another antibody which binds to a homologous polypeptide and might preferentially trigger a false-positive result.

In particular, for the differential diagnosis, in which the aim may be to distinguish in a patient with neurological symptoms, whether he suffers from an autoimmunity-caused encephalitis or an encephalitis caused by infection, preferably a limbic encephalitis, it is advantageous to simultaneously capture and/or detect antibodies against NMDAR on the one hand and antibodies against BoDV-1-N, BoDV-1-P, VSBV-N, VSBV-P or other viruses or antigens derived therefrom which cause similar or confusable symptoms in an infection. A carrier suitable for this purpose can comprise, in addition to NMDAR and/or at least one antigen from the group comprising BoDV-1-N, BoDV-1-P, VSBV-N, VSBV-P, at least one antigen of another virus, preferably several antigens of other viruses. Also useful are other antigens with which further autoantibodies can be detected. In this case, it is most likely that a positive result with an antigen can be achieved within one test procedure and that one does not have to work with an exclusion-based diagnosis.

In a particularly preferred embodiment, the term "bind specifically", as used herein, means, in the case of an antibody, that it binds against the corresponding antigen in a binding reaction characterized by a dissociation constant which is $1\times10^{-5}$ M, more preferably $1\times10^{-7}$ M, more preferably $1\times10^{-8}$ M, more preferably $1\times10^{-9}$ M, more preferably $1\times10^{-10}$ M, more preferably $1\times10^{-11}$ M, more preferably $1\times10^{-12}$ M or a stronger binding reaction. Preferably, the dissociation constant is, in this connection, measured by surface plasmon resonance using a Biacore instrument at 25° C. and in PBS buffer at pH 7 and calculated using the software supplied by the manufacturer.

In a particularly preferred embodiment, the means for the capture of an antibody is a polypeptide having epitopes recognized by the antibody to be detected or variants thereof. Alternatively, it is also possible to use peptidomimetics of such polypeptides having appropriate binding capacity with respect to the antibody to be detected, for example peptoids, beta-peptides and peptides containing unnatural amino acids. A person skilled in the art is familiar with such molecules and their design (Pelay Gimeno M, Glas A, Koch O, Grossmann T N (2015). "Structure-based design of inhibitors of protein-protein interactions: Mimicking peptide binding epitopes". Angewandte Chemie International Edition. 54 (31): 8896-8927). Exemplary polypeptides as capture means encompass SEQ ID NO:7 for the capture of antibodies against the NR1 subunit of the human NMDA receptor, its dimers or complexes thereof with other subunits of the NMDA receptor such as NR2A (SEQ ID NO:3 from EP2057466) or NR2B (SEQ ID NO:1 from EP2057466) or NR2C (SEQ ID NO:5 from EP2057466 B1) for the capture of antibodies against the NMDA receptor, SEQ ID NO:1 and/or SEQ ID NO:2 from EP2863231 A1 for the capture of antibodies against human GABA(A) receptor, SEQ ID NO:1, SEQ ID NO:2 or SEQ ID NO:3 from EP2483417 B1 for the capture of antibodies against human GABA(B) receptor, SEQ ID NO:1, SEQ ID NO:2, SEQ ID NO:3 or SEQ ID NO:4 from WO2014/041035A1 for the capture of antibodies against DPPX, SEQ ID NO:2 from U.S. Pat. No. 9,250,250 BB for the capture of antibodies against Lgl1 or CASPR2 (U.S. Pat. No. 9,250,250 BB), SEQ ID NO:1 from EP2905622 A1 for the capture of antibodies against IGLON5, SEQ ID NO:1 from EP17001205 for the capture of antibodies against NSF, SEQ ID NO:3 from EP17001205 for the capture of antibodies against STX1V, SEQ ID NO:6 from EP17001205 for the capture of antibodies against VAMP2, the sequence Q9Y6R1 from Uniprot (cf. EP3026434 A1) for the capture of antibodies against NBC1, O75955 (flotillin1, Uniprot) and/or Q14254 (flotillin2, Uniprot) (cf. EP3101424 A1) for the capture of antibodies against flotillin and Q14643 (Uniprot) (cf. EP3018478 A1) for the capture of antibodies against ITPR and, in each case, variants thereof. The capture means can be the virus itself, preferably in the form of a cell, more preferably a mammalian cell, which is infected with the virus. The cell is preferably isolated and/or purified.

It is possible to carry out the teaching according to the invention not only by using the wild-type sequences of the specified polypeptides or the reference sequences, as specified here, possibly implicitly, in the form of SEQ ID NOs, referred to collectively from now on as "full-length polypeptide", or database codes or in some other way, but also by using variants of said sequences.

In a particularly preferred embodiment, the term "variant", as used herein, means, in this connection, at least one fragment of the full-length polypeptide that is truncated with respect to the full-length polypeptide by one or more than one amino acid at the C- and/or N-terminal end. Such a fragment can contain a length of 5, 6, 7, 8, 10, 12, 15, 20, 25, 50, 75, 100, 150, 200, 250, 300, 400, 500 or 600 successive amino acids from the sequence of the full-length polypeptide, preferably 10 or more.

In a further preferred embodiment, the term "variant", as used herein, encompasses not only a fragment, but also a polypeptide having amino acid sequences with, in order of increasing preference, at least 40, 50, 60, 70, 75, 80, 85, 90, 92, 94, 95, 96, 97, 98 or 99% sequence identity in relation to the full-length polypeptide or to the fragment thereof, with no deletion or non-conservative substitution of any amino acid essential for biological activity, for example the capacity of an antigen to bind to an antibody specific for the full-length polypeptide antigen. The prior art discloses methods for establishing the sequence identity of amino acid sequences, for example in Arthur Lesk (2008), Introduction to Bioinformatics, Oxford University Press, 2008, third edition. In a preferred embodiment, use is made of the ClustalW software (Larkin, M. A., Blackshields, G., Brown, N. P., Chenna, R., McGettigan, P. A., McWilliam, H., Valentin, F., Wallace, I. M., Wilm, A., Lopez, R., Thompson, J. D., Gibson, T. J., Higgins, D. G. (2007). Clustal W and Clustal X version 2.0. Bioinformatics, 23, 2947-2948) using the standard settings for this purpose.

In addition, a polypeptide used according to the invention or a variant thereof can have chemical modifications, for example isotope label, covalent modifications such as glycosylation, phosphorylation, acetylation, decarboxylation, citrullination, methylation, hydroxylation, etc.

Variants can also be fusion proteins with other known polypeptides or variants thereof, preferably with a purification tag, even more preferably from the group comprising His-tag, thioredoxin, maltose-binding protein, streptavidin, glutathione S-transferase or a variant thereof, and be or comprise active parts or domains, preferably with a sequence identity of at least 70, 75, 80, 85, 90, 92, 94, 95, 96, 97, 98 or 99% in relation to the full-length polypeptide. In a preferred embodiment, the term "active parts or domains" is understood to mean a fragment of the full-length polypeptide or a variant which, in both cases, retains at least some of the biological activity of the full-length polypeptide.

It is essential that the variant of the full-length polypeptide has biological activity. In a preferred embodiment, biological activity is the capacity of an antigen to capture an antibody which binds specifically to the full-length polypeptide. A variant of BoDV-1-N, BoDV-1-P, BoDV-1-X, VSBV-N, VSBV-P and VSBV-X thus has the capacity to capture an antibody against BoDV-1-N, BoDV-1-P, BoDV-1-X, VSBV-N, VSBV-P and VSBV-X, respectively. Preferably, the antibody is one which occurs specifically in the blood of a patient who is suffering from a certain disease. For example, a variant of an antigen for the capture of an antibody against a bornavirus has the capacity to specifically bind an antibody from a patient against said antigen of the bornavirus. Whether this is the case can be determined using an immunoblot, as described in Example 1.

Variants according to the invention encompass, for example, SEQ ID NO:1 (variants of VSBV-N), SEQ ID NO:3 (VSBV-P), SEQ ID NO:4 (BoDV-1-N) and SEQ ID NO:5 (BoDV-1-P).

In a preferred embodiment, the capture means is an isolated and/or purified polypeptide which is particularly preferably recombinant. An "isolated" polypeptide can, in this connection, be understood to mean that the polypeptide was removed from its natural environment. A "purified" polypeptide is, in a preferred embodiment, understood to mean a polypeptide which was enriched with respect to the concentration and/or purity in its natural environment using chromatographic methods preferably selected from the group comprising affinity chromatography, gel-filtration chromatography and ion-exchange chromatography. In a particularly preferred embodiment, a polypeptide is purified when it has a purity of at least 40, 50, 60, 70, 80, 90, 95, 98, 99 or 99.5%, and this can be assessed visually or, preferably, by measurement of the intensity of bands on an SDS-PAGE gel after Coomassie staining.

A polypeptide can be provided in the form of a tissue or a cell, preferably a recombinant tissue or a recombinant cell. The cell is preferably a eukaryotic cell, more preferably an insect, plant or mammalian cell, even more preferably a mammalian cell, most preferably a human cell.

A polypeptide can be provided in folded form or in unfolded form. Preferably, folding is measured by means of CD spectroscopy in a buffer which allows the measurement and in which the protein can assume its three-dimensional folding (cf. for example Banaszak L. J. (2008), Foundations of Structural Biology, Academics Press, or Teng Q. (2013), Structural Biology: Practical Applications, Springer), for example in 10 mM sodium phosphate at pH 7. Preferably, the protein assumes folding which is recognized by an antibody to be detected.

A capture means is immobilized, preferably on a carrier, even more preferably via a covalent or non-covalent bond.

In a preferred embodiment, an antibody is, after capture, detected by a method from the group comprising immunodiffusion, immunoelectrophoresis, light scattering, agglutination, radioactivity, enzymatic activity, (electro)chemiluminescence and immunofluorescence. In the case of a detection by radioactivity, enzymatic activity, (electro) chemiluminescence and immunofluorescence, a detectable label can be used. It is preferably attached to a secondary antibody which binds to the antibody to be detected. Detection methods are, for example, described in Zane, H. D. (2001), Immunology—Theoretical & Practical Concepts in Laboratory Medicine, W. B. Saunders Company, particularly in chapter 14.

In a preferred embodiment, the antibody to be detected is an antibody from the group comprising immunoglobulin class G (IgG), immunoglobulin class M (IgM) and immunoglobulin class A (IgA), preferably G or M, even more preferably G. In a further preferred embodiment, two or more classes of antibodies from the group comprising immunoglobulin class G, immunoglobulin class M and immunoglobulin class A, preferably G and M, are detected.

The antibody to be detected can be quantified. In a preferred embodiment, the antibody to be detected is detected and preferably quantified on more than one day. Even more preferably, the antibody is one of class G (IgG). In this way, it is possible to follow the course of the titre. In this case, an IgG titre which rises over time allows the identification of an active infection with a bornavirus and the differentiation of an active infection with a bornavirus from a passive immunization or a contact, respectively an infection, with the pathogen from further in the past.

In a preferred embodiment, the carrier is selected from the group comprising a membrane-based immunoblot, preferably a Western blot, lateral flow assay or a line blot, one or more than one bead, a biochip arranged for immunofluorescence, and an ELISA microtiter plate.

The invention provides a kit which comprises the carrier according to the invention, and in addition optionally instructions and/or buffers and reagents, preferably from the group comprising a wash solution, a solution comprising a means for the detection of a captured antibody and a solution comprising a positive control. Instead of a solution, the particular reagent can also be provided in dry form, for example as a powder, preferably with a solution in which it can be dissolved if necessary. As positive control, it is possible to use an antibody to be detected or a variant thereof that binds specifically to the antigen to which the antibody binds. Preferably, the carrier comprises a control for the detection of the presence of a sample, preferably a serum sample. For example, a protein present in every serum sample can be detected in order to confirm the presence of a serum sample. The means used for the detection of a captured antibody is preferably a secondary antibody having a detectable label.

In the present patent application, novel polypeptides and/or nucleic acids are listed. They have the following sequences:

```
(VSBV-N (40 kDa, His-tag))
                                         SEQ ID NO: 1
MNITMPPKRRLLEDPDVMDDQEPEPTSPPMPKLPGKFLQYTVGGSDPHPG

IGEEKDIKHNAVALLDSSRRDMFHPVTPSLVFLCLLIPGLHAAFLHGGVP

KESYLSTPISRGEQTFVKVSRFYGERTASRELTELEISSIFNHCCSLLIG

VVIGSSAKIRAGAEQIKKRFKTLMASLNRPSHGETATLLQMFNPHEAIDW

INGQPWVGSLVLSLLTTDFESPGKEFMDQIKLVASYAQMTTYTTIKEYLA

ECMDATLTIPAVAHEIREFLEISAKLKNEHAELFPFLGAIRHPDAIKLAP

RSFPNLASAAFYWSKKENPTMAGYRASTIQPGATVKETQLARYRRREVSR

GEDGAELSGEISDIMKMIGVTGLVLEHHHHHH (VSBV-N peptide (30 kDa, His-GST-tag))
                                         SEQ ID NO: 2
MSHHHHHHHHMSPILGYWKIKGLVQPTRLLLEYLEEKYEEHLYERDEGDK

WRNKKFELGLEFPNLPYYIDGDVKLTQSMAIIRYIADKHNMLGGCPKERA

EISMLEGAVLDIRYGVSRIAYSKDFETLKVDFLSKLPEMLKMFEDRLCHK

TYLNGDHVTHPDFMLYDALDVVLYMDPMCLDAFPKLVCFKKRIEAIPQID

KYLKSSKYIAWPLQGWQATFGGGDHPPKLEVLFQGPAMFVKVSRFYGERT

ASR (VSBV-P (23 kDa, His-tag))
                                         SEQ ID NO: 3
MASRPSSLVESLEDEESLQTPRRVRSRSPRPKRIPQDALTQPVDRLLKNI

KKNPSMISDPEQRTGREQLSNDELIKQLVTELAENSMIEAEGLRGALDDI

SSKVDSGLESISSLQVETLQTVQKTDYADSIKTLGENIKVLDRSMKTMME

TMRLMMEKIDLLYASTAIGQSNTPMLPSHPAQPRLYPTLPSAPTADEWDI

LPLEHHHHHH (BoDV-1-N (40 kDa, His-tag))
                                         SEQ ID NO: 4
MNITMPPKRRLVDDADAMEDQDLYEPPASLPKLPGKFLQYTVGGSDPHPG

IGHEKDIRQNAVALLDQSRRDMFHTVTPSLVFLCLLIPGLHAAFVHGGVP

RESYLSTPVTRGEQTVVKTAKFYGEKTTQRDLTELEISSIFSHCCSLLIG

VVIGSSSKIKAGAEQIKKRFKTMMAALNRPSHGETATLLQMFNPHEAIDW

INGQPWVGSFVLSLLTTDFESPGKEFMDQIKLVASYAQMTTYTTIKEYLA

ECMDATLTIPVVAYEIRDFLEVSAKLKEEHADLFPFLGAIRHPDAIKLAP

RSFPNLASAAFYWSKKENPTMAGYRASTIQPGASVKETQLARYRRREISR

GEDGAELSGEVSAIMKMIGVTGLNLEHHHHHH (BoDV-1-P (23 kDa, His-tag))
                                         SEQ ID NO: 5
MATRPSSLVDSLEDEEDPQTLRRERSGSPRPRKIPRNALTQPVDQLLKDL

RKNPSMISDPDQRTGREQLSNDELIKKLVTELAENSMIEAEEVRGTLGDI

SARIEAGFESLSALQVETIQTAQRCDHSDSIRILGENIKILDRSMKTMME

TMKLMMEKVDLLYASTAVGTSAPMLPSHPAPPRIYPQLPSAPTADEWDII

PLEHHHHHH (VSBV-N peptide, amino acids 116-130 of A0A0H5BD6)
                                         SEQ ID NO: 6
FVKVSRFYGERTASR (NR1 subunit of the NMDAR receptor)
                                         SEQ ID NO: 7
MSTMHLLTFALLFSCSFARAACDPKIVNIGAVLSTRKHEQMFREAVNQAN

KRHGSWKIQLNATSVTHKPNAIQMALSVCEDLISSQVYAILVSHPPTPND

HFTPTPVSYTAGFYRIPVLGLTTRMSIYSDKSIHLSFLRTVPPYSHQSSV

WFEMMRVYNWNHIILLVSDDHEGRAAQKRLETLLEERESKAEKVLQFDPG

TKNVTALLMEARELEARVIILSASEDDAATVYRAAAMLNMTGSGYVWLVG

EREISGNALRYAPDGIIGLQLINGKNESAHISDAVGVVAQAVHELLEKEN

ITDPPRGCVGNTNIWKIGPLFKRVLMSSKYADGVTGRVEFNEDGDRKFAN

YSIMNLQNRKLVQVGIYNGTHVIPNDRKIIWPGGETEKPRGYQMSTRLKI
```

```
-continued
VTIHQEPFVYVKPTMSDGTCKEEFTVNGDPVKKVICTGPNDTSPGSPRHT

VPQCCYGFCIDLLIKLARTMNFTYEVHLVADGKFGTQERVNNSNKKEWNG

MMGELLSGQADMIVAPLTINNERAQYIEFSKPFKYQGLTILVKKEIPRST

LDSFMQPFQSTLWLLVGLSVHVVAVMLYLLDRFSPFGRFKVNSEEEEEDA

LTLSSAMWFSWGVLLNSGIGEGAPRSFSARILGMVWAGFAMIIVASYTAN

LAAFLVLDRPEERITGINDPRLRNPSDKFIYATVKQSSVDIYFRRQVELS

TMYRHMEKHNYESAAEAIQAVRDNKLHAFIWDSAVLEFEASQKCDLVTTG

ELFFRSGFGIGMRKDSPWKQNVSLSILKSHENGFMEDLDKTWVRYQECDS

RSNAPATLTFENMAGVFMLVAGGIVAGIFLIFIEIAYKRHKDARRKQMQL

AFAAVNVWRKNLQDRKSGRAEPDPKKKATFRAITSTLASSFKRRRSSKDT

STGGGRGALQNQKDTVLPRRAIEREEGQLQLCSRHRES
```

The invention will be elucidated below by means of exemplary embodiments with reference to the figures. The embodiments described are, in every respect, merely exemplary and not to be understood as restrictive, and various combinations of the stated features are encompassed by the scope of the invention.

FIG. 1 shows the structure of a line blot strip with bornaviral antigens, as prepared and used in Example 1.

FIG. 2 shows a line blot strip with bornaviral antigens, as prepared in Example 1, after the incubation as per Example 1.

Figure 3:
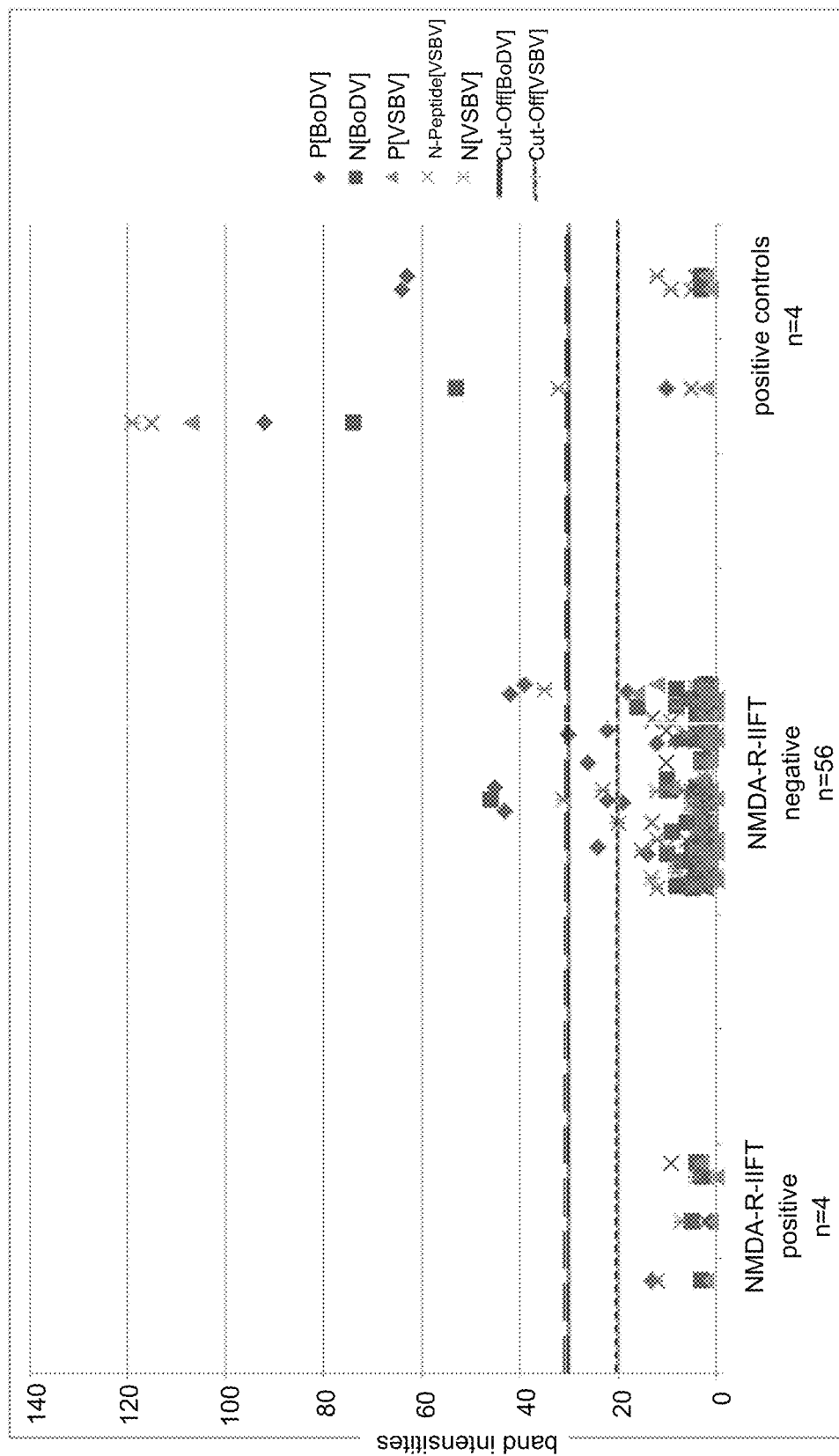
FIG. 3 shows the results of the testing of samples from patients with limbic encephalitis using a line blot strip prepared in Example 1.

FIG. 3 shows the results of the testing of samples from patients with limbic encephalitis using a line blot strip prepared in Example 1.

Figure 4:
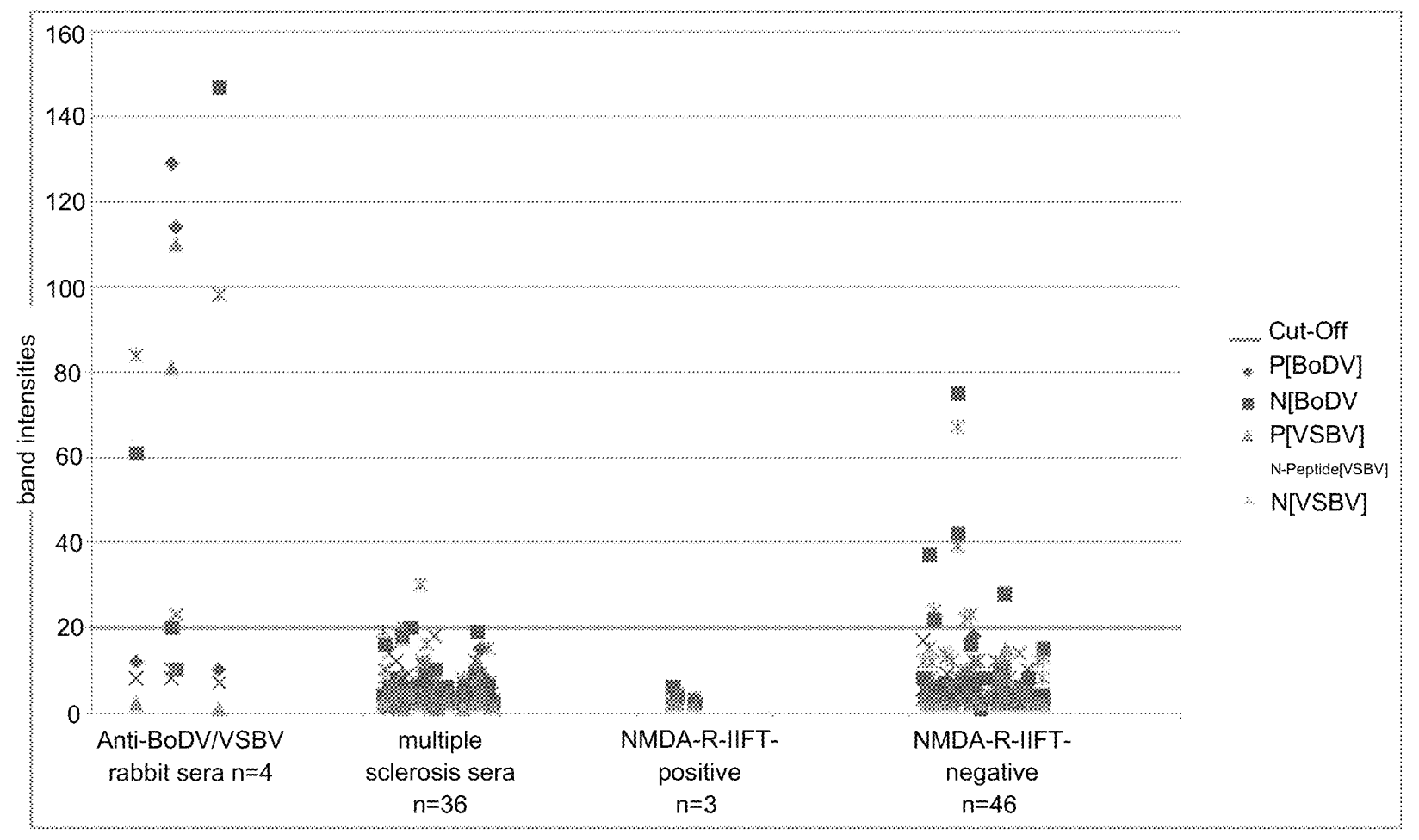

FIG. 4 shows the results of the testing of samples from patients with limbic encephalitis using a further line blot strip prepared in Example 1.

Figure 5:
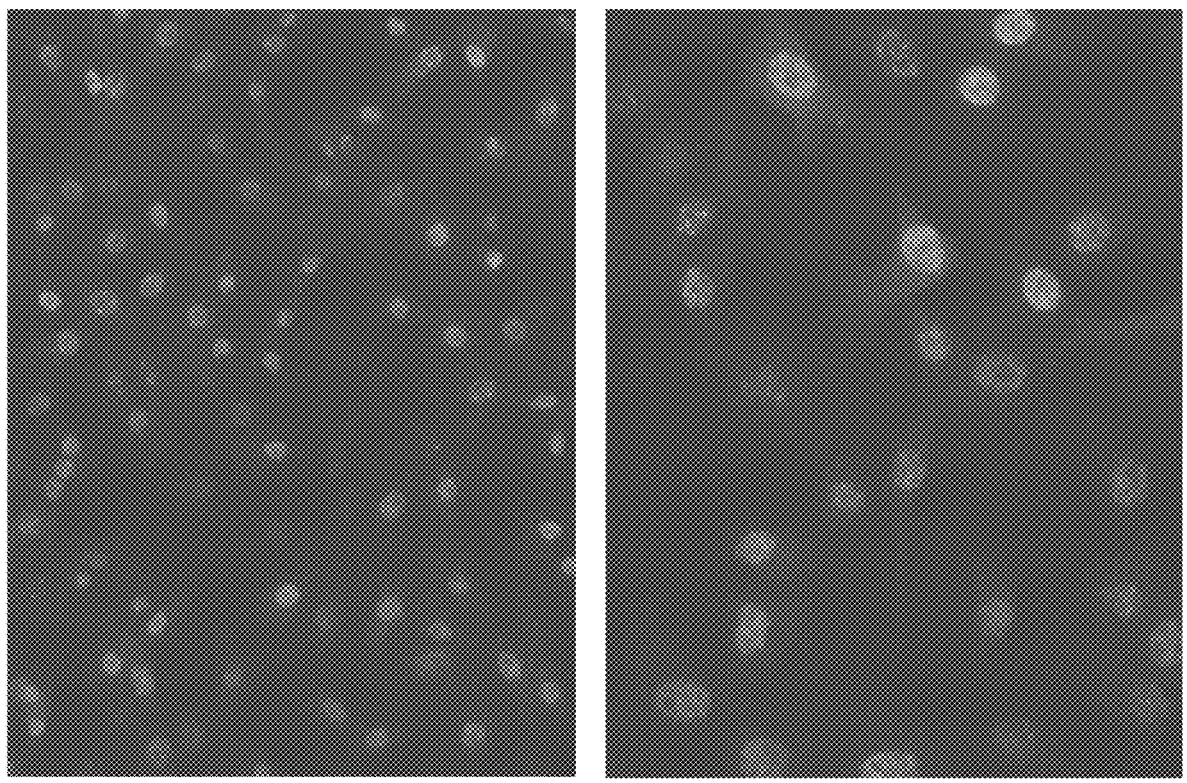
FIG. 5 shows the result of the testing of a sample from a transplantation patient by means of immunofluorescence—see Example 2—in two different magnifications (left 200×, right 400×).

FIG. 5 shows the result of the testing of a sample from a transplantation patient by means of immunofluorescence—see Example 2—in two different magnifications (left 200×, right 400×).

FIG. 6 shows the testing of samples from a transplantation patient using a line blot strip with bornaviral antigens that was prepared as per Example 1; see Example 2.

EXAMPLES

Example 1: Membrane-Based Antibody Detection Against Variegated Squirrel Bornavirus I (VSBV1) and Mammalian Boravirus I (BoDV-1)

1.1. Preparation of a EUROLINE Anti-Bornavirus Profile
Coating of the Antigens on Nitrocellulose Membrane:
VSBV-N protein (SEQ ID NO:1), VSBV-N peptide (SEQ ID NO:2), BoDV-1-N protein (SEQ ID NO:4), BoDV-1-P protein (SEQ ID NO:5) and VSBV-P protein (SEQ ID NO:3) were fused with a His-tag by recombinant means in *E. coli* and purified by affinity chromatography using standard protocols. The purified proteins were stored in a frozen state (−70° C.) and thawed prior to the coating process.

For the preparation of the EUROLINE Anti-Bornavirus Profile a, the antigens were coated in two dilutions in each case (with concentrations from 9 μg/ml to 59 μg/ml that are variable for each antigen).

On a following second EUROLINE Anti-Bornavirus Profile b, the concentrations of the BoDV-1 antigens were reduced by 50% in each case. The diluted antigens were coated by machine using a contact tip dispenser (see: Raphael Wong, Harley Tse: Lateral Flow Immunoassay; Humana Press; 2008, page 137). FIG. 1 shows the structure of the EUROLINE, where 1 refers to the higher antigen concentration and 2 refers to the lower antigen concentration.

Thereafter, the coated membranes were blocked, rinsed, dried, and stored at −20° C. for further use.

Sticking of the Coatings on Carrier Film:

To create the EUROLINE Anti-Bornavirus Profile, lines of each antigen were fixed on plastics films. This was followed by division into individual test strips.

1.2. Performance of Immunoassays Using the EUROLINE

Incubation of Serum Samples:

1. Pretreatment:

In accordance with the number of patient samples to be tested, the incubation troughs were filled with, in each case, 1.5 ml of universal buffer (ZD 1100-1050, EUROIMMUN AG) diluted ready for use. The required quantity of test strips were removed from the package using tweezers and placed directly into, in each case, a buffer-filled incubation trough and incubated on a rocker shaker at room temperature for 15 minutes. Thereafter, the liquid was completely removed from the troughs.

2. Sample Incubation:

1.5 ml of the patient sample diluted 1:51 in universal buffer were filled into each incubation trough filled with a test strip, and incubated on a rocker shaker at room temperature (+23° C.) for 30 minutes.

3. Washing:

The liquid was completely removed from each trough and washing was carried out on a rocker shaker for 3×5 minutes with, in each case, 1.5 ml of universal buffer diluted ready for use.

4. Conjugate Incubation:

1.5 ml in each case of enzyme conjugate (alkaline phosphatase-labelled anti-human IgG; AE 142-1030, EUROIMMUN AG) diluted ready for use were pipetted into the incubation troughs and incubated on a rocker shaker at room temperature (+23° C.) for 30 minutes.

5. Washing:

The liquid was completely removed from the troughs. Step 3. was carried out again.

6. Substrate incubation:

1.5 ml in each case of substrate solution (ZW 1020-0130, EUROIMMUN AG) were pipetted into the incubation troughs. This was followed by a 10-minute incubation on a rocker shaker at room temperature (+23° C.).

7. Stopping:

The liquid from each trough was completely removed and each test strip was rinsed for 3×1 minute with distilled or deionized water.

8. Evaluation:

The test strips were air-dried and evaluated.

Incubation of Liquor Samples:

1. Pretreatment:

In accordance with the number of patient samples to be tested, the incubation troughs were filled with, in each case, 1.5 ml of universal buffer. The required quantity of test strips were removed from the package using tweezers and placed directly into, in each case, a buffer-filled incubation trough. Incubation was carried out on a rocker shaker at room temperature (+23° C.) for 15 minutes. Thereafter, the liquid was completely removed from the troughs.

2. Sample Incubation:

1.0 ml of the diluted patient samples (liquor dilution factor 1:4, diluted in universal buffer) was filled into each incubation trough filled with a test strip. This was followed by a three-hour incubation on a rocker shaker at room temperature (+23° C.).

3. Washing:

The liquid was completely removed from each trough and washing was carried out on a rocker shaker for 3×5 minutes with, in each case, 1.5 ml of wash buffer diluted ready for use.

4. Conjugate Incubation:

1.5 ml in each case of enzyme conjugate (alkaline phosphatase-labelled anti-human IgG) diluted ready for use were pipetted into the incubation troughs. Incubation was carried out on a rocker shaker at room temperature (+23° C.) for one hour.

5. Washing:

The liquid was completely removed from the troughs, and washing was carried out as above.

6. Substrate Incubation:

1.5 ml in each case of substrate solution were pipetted into the incubation troughs. Incubation was carried out on a rocker shaker at room temperature (+23° C.) for 20 minutes.

7. Stopping:

The liquid was completely removed from each trough and each test strip was rinsed for 3×1 minute with distilled or deionized water.

8. Evaluation:

The test strips were air-dried and evaluated.

FIG. 2 shows an exemplary strip after incubation.

Evaluation:

The intensities measured using the EUROLINEScan software (EUROIMMUN Medizinische Labordiagnostika AG, Lubeck) were evaluated by an experienced member of staff, taking account of the criterion stated below. For a positive result, the specific antigen coating in each case (the less concentrated one of the two coated dilutions) had to react above the cut-off.

For the EUROLINE Anti-Bornavirus Profile a, the cut-off was defined as follows. The numbers correspond to the band intensities measured in the EUROLINE-Scan:

BoDV-1 antigens: 0-23=negative; 24-30=borderline; >30=positive

VSBV antigens: 0-13=negative; 14-20=borderline; >20=positive

For the EUROLINE Anti-Bornavirus Profile b, the following cut-off was defined:

All antigens: 0-13=negative; 14-20=borderline; >20=positive 1.3. Results Using Various Sample Groups:

NMDA-R-IFT-Precharacterized Patient Sera:

Anonymized serum samples from patients suffering from symptoms of limbic encephalitises were tested.

Altogether, incubation was carried out of n=60 samples in a first experiment on the EUROLINE Anti-Bornavirus Profile a and a further n=49 samples in a second study on the EUROLINE Anti-Bornavirus Profile b, which meet these requirements. The samples were examined for the presence of autoantibodies against the NMDA receptor by means of immunofluorescence (product FA 112d-1003-51, EUROIMMUN Medizinische Labordiagnostika AG). Thereafter, they were tested on the EUROLINE Anti-Bornavirus Profile, as prepared under 1.1.

In the case of immunofluorescence examination, n=7 samples from altogether n=109 samples reacted positively in the anti-NMDA-R IFT. For these patients, the encephalitis can thus be attributed to autoantibodies against the NMDA receptor. None of the n=7 NMDA-R-IFT-positive sera reacted positively on the EUROLINE Anti-Bornavirus Profile.

For the remaining n=102 patients, whose samples reacted negatively in the anti-NMDA-R IFT, the cause of disease remains unresolved. For this group, bornavirus infections, inter alia, can be expected as a possible cause.

From these n=102 samples, altogether n=14 samples reacted positively with at least one bornavirus antigen (of these, n=7 in the first experiment and n=7 in the second experiment). This corresponds to 13.73% of encephalitises which might be caused by a bornavirus infection.

Sera from Patients with Multiple Sclerosis

In the case of encephalomyelitis disseminata, the exact causes are still unclear, too. However, this encephalitis affects a different region of the CNS than a limbic encephalitis and serves as a control group. What were tested were n=36 samples on the EUROLINE Anti-Bornavirus Profile b, of which n=1 serum reacted positively with the EUROLINE Anti-Bornavirus Profile.

Positive Controls:

As positive controls, the following samples were used on the EUROLINE Anti-Bornavirus Profile a:

n=1 anti-VSBV-positive liquor n=1 serum from a psychosis patient n=2 serologically precharacterized BoDV-1-positive sera The following positive controls were incubated on the EUROLINE Anti-Bornavirus Profile b:

n=4 polyclonal rabbit sera (one against VSBV-N, one against VSBV-P, one against BoDV-1-N, one against BoDV-1-P, prepared by immunization of rabbits as per standard protocols using VSBV-N protein, VSBV-N peptide, BoDV-1-N protein, BoDV-1-P protein and VSBV-P protein having the sequences stated in section 1.1. of the example section)

From these altogether n=8 sera, all reacted positively with at least one antigen on the EUROLINE Anti-Bornavirus Profile; the polyclonal antibodies recognized in each case the corresponding coated antigen.

Negative Control:

Liquor samples not originating from patients with suspected limbic encephalitis were used. None of the liquor samples reacted positively with the EUROLINE Anti-Bornavirus Profile, showing the specificity of the test strip under these incubation conditions.

The results with the EUROLINE Anti-Bornavirus Profile a are depicted in FIG. 3, and the results with the EUROLINE Anti-Bornavirus Profile b are depicted in FIG. 4. They illustrate that no patient suffering from NMDAR-receptor encephalitis and associated PNS or associated cancer types had antibodies against BoDV-1 or VSBV-1.

Example 2: Detection of Antibodies Against Bornavirus in a Sample from a Patient with Post-Transplantation Complications Patients:

Patient 1 received an organ donation from a clinically normal donor. After the transplantation, the recipient developed neurological complications which culminated in an encephalitis.

As negative controls, 264 blood samples from healthy blood donors were tested.

Antibody Detection:

Serum samples from the patient were examined using the anti-chikungunya virus IIFT from EUROIMMUN Medizinische Labordiagnostika AG (order number FI 293a-1005 G), with the difference that the antigen used was not the one used in the aforementioned test (CHIKV-infected Vero cells), but the BoDV-1-infected cell line CRFK 227, as described in Hoffmann et al. (2015) A variegated squirrel bornavirus associated with fatal human encephalitis, N Engl J Med 2015; 373, pages 154-162, and in the associated supplementary appendix (page 19). The protocol in the instructions from the manufacturer was followed.

Samples collected regularly from day 72 after the transplantation were tested for the presence of antibodies against BoDV-1-P, BoDV-1-N, VSBV-P and VSBV-N. This involved using the blots described in Example 1 and carrying out the detection as in said example.

Results:

Some of the consecutive samples from Patient 1 were examined using the indirect immunofluorescence test. All the samples showed a positive reactivity, i.e. it was possible to identify the specific fluorescence pattern in the bornavirus-infected cells. This is depicted by way of example in FIG. 5. In the cell nuclei of the infected cells, there is fluorescence of individual granules to multiple granules that contain the virus antigen. This confirms the presence of bornavirus-specific antibodies in the patient sample.

The testing of the blood samples in the line blot showed that there were still no detectable antibodies on day 72 after the transplantation (FIG. 6). From day 84, it was possible to detect antibodies against BoDV-1-P, and from day 382, it was also possible to detect antibodies against VSBV-N. 98.5% of the blood donors were negative as per IIFT.

CONCLUSION

It can therefore be concluded that the organ donor was latently infected with BoDV-1 without the occurrence of a clinically apparent infection. The transplantation caused an outbreak of the infection in the organ recipient, presumably because of the immunosuppressive treatment.

Example 3: Limbic Encephalitis Due to Infection with VSBV-1

Methods

Case Study

In July 2013, a 45-year-old animal keeper from Schleswig-Holstein developed fever, dysphonia, coughing, pharyngitis, vertigo and paresthesia below her eye. These symptoms were followed by ataxia, coma and pituitary gland insufficiency. The patient had no known previous conditions. Analysis of the CSF had shown a lymphocytic pleocytosis. The inflammation parameters in the peripheral blood were elevated, with relative neutrophilia and lymphopenia. An initial MRI examination of the head showed normal results. A follow-up MRI examination 3 weeks later showed lesions with a bilateral limbic distribution (medial temporal lobes, anterior cingulum, insula, hippocampus, hypothalamus, periventricular tectum), in the basal ganglia and in the upper spinal cord. Morphologically, limbic encephalitis was diagnosed with progression within one week. Extensive laboratory tests with respect to infections of the central nervous system and autoimmune diseases showed normal results. No underlying neoplasia was discovered. Repeated electroencephalograms showed general slow activity and non-convulsive epileptic seizures. Microscopy, culture or PCR did not show any neurotropic bacteria, fungi, parasites or viruses. By means of immunohistochemistry, it was possible to rule out a Creutzfeldt-Jakob disease. Owing to bilateral pneumonia, the patient required artificial respiration, and she was treated with a broad anti-infection therapy (including acydovir), anticonvulsants and with steroids in the later course of the disease. Within 3 months after the onset of the symptoms, she ultimately died of myeloencephalitis of an aetiology which was undetermined at that time.

PCR

Stored, frozen CSF and formalin-fixed, paraffin-embedded brain tissue, myocardium, lung tissue, kidney tissue, liver tissue, spleen tissue, pancreatic tissue, bone marrow and intestinal tissue were provided for the analyses. A VSBV-1-specific real-time RT-PCR was carried out as described in Hoffmann et al. (2015).

Immunohistochemistry

Polyclonal antisera against N and P proteins of VSBV-1 and BoDV-1 were obtained from rabbits which had been immunized with the respective recombinant antigen, and they were purified by means of protein A affinity chromatography (Davids Biotechnologie, Regensburg, Germany). The reactivity of the rabbit antisera and pre-immune sera was tested by means of an immunofluorescence antibody test (IFAT) and with the aid of the bornavirus immunblots described in Example 1. Ten unrelated human brain-tissue samples were used as negative controls. After pretreatment with proteinase K and blocking of endogenous peroxidase, the FFPE sections from the patient were incubated with the antisera (1:1000-1:5000 in PBS, overnight at room temperature). Thereafter, they were incubated with a goat anti-rabbit biotinylated polymer antibody, a streptavidin-horseradish peroxidase complex and with the 3-amino-9-ethylcarbazole (AEC) substrate (DCS, Hamburg, Germany).

Serological Tests

For the detection of bornavirus-specific IgG antibodies in the serum and CSF, a cell line stably infected with BoDV-1 was used for a standard indirect immunofluorescence test (IFAT) (Hoffmann et al., 2015); in addition, an ELISA and an immunoblot were developed.

For the VSBV-1 IgG ELISA, the sequences of VSBV-1 N and P protein were cloned and expressed in the form of fusion proteins with maltose-binding protein (MBP) in the $E.\ coli$ strain BL21 GOLD (DE3) (Novagen-Merck, Darmstadt, Germany). The protein was purified and eluted by means of amylose affinity chromatography. The N-terminal MBP-tag was cleaved off overnight at 4° C. by means of 3C protease. After removal of the protease, the protein sample was further purified by means of gel-filtration chromatography (Superdex 200, Sigma-Aldrich, Munich, Germany). Microtiter plates (Polysorp, Nunc, Roskilde, Denmark) were coated overnight at 4° C. with 2 μg/ml VSBV-1 N or P protein. After blocking with 6% BSA, human serum diluted in 1% BSA dilution solution was added. After a two-hour incubation at 37° C., 100 μl of anti-human IgG (Dako Cytomation, Hamburg, Germany, diluted 1:6000) were added, and the plates were incubated at 37° C. for one hour. After 5 minutes of incubation at room temperature with 3,3',5,5'-tetramethylbenzidine, the reaction was stopped. Lastly, the optical density (OD) was measured at 450 nm (reference: 620 nm). The final OD value for each serum sample was measured as the difference between the wells containing VSBV-1 N or P protein and the wells containing MBP. The final OD values for a serum dilution of 1:400 were considered positive when the averaged OD exceeded the averaged OD plus three times the standard deviation which were obtained with control samples from 200 healthy blood donors.

For the bornavirus IgG immunoblot, the strips prepared in Example 1 were used. They were incubated at room temperature with serum (30 minutes, 1:51) or with CSF (3 hours, 1:4), followed by an incubation with alkaline phosphatase conjugate (30 min or 1 hour, 1:10 in each case), and nitro blue tetrazolium chloride as substrate (10 or 20 min). The intensities of the detected antibodies were evaluated automatically using the EuroLineScan software (EUROIMMUN AG, Lübeck, Germany). For the validation, samples from 150 healthy blood donors were tested.

Results

Serology with Samples from the Encephalitis Patient

Bornavirus-specific IgG antibodies were detected in high concentration in the CSF of the patient, in the form of a nuclear pattern by immunofluorescence (IgG end point titre 1:2560) and by ELISA. A strong IgG reactivity was shown on the immunoblot against VSBV-1 N polypeptide, and to a lesser extent against VSBV-1-P and BoDV-1-P antigens (Table 1).

TABLE 1

Serological test results for the encephalitis patient and the animal keepers.

| Category | | Age | Sex | IgG immunoblot* | | | | BoDV-1 IgG IFAT | VSBV-1 IgG ELISA§ | | Contact with variegated squirrels |
|---|---|---|---|---|---|---|---|---|---|---|---|
| | | | | BoDV-1-P | BoDV-1-N | VSBV-P | VSBV-N | | VSBV-P | VSBV-N | |
| Encephalitis patient (CSF) | | 45 | F | + | o | + | + | 1:2560 | pos | pos | regular |
| 14 animal keepers (serum) | | 44 | F | o | o | o | (+) | neg | neg | neg | regular |
| | | 32 | M | o | o | o | o | neg | neg | neg | regular |
| | | 25 | F | o | + | o | (+) | neg | neg | neg | seldom |
| | | 33 | F | o | o | o | o | neg | neg | neg | occasional |
| | | 26 | F | o | o | o | (+) | 1:160# | neg | neg | occasional |
| | | 27 | M | o | + | o | o | neg | neg | neg | occasional |
| | | 29 | F | o | o | o | o | neg | neg | neg | seldom |
| | | 48 | F | o | (+) | o | + | 1:40 | neg | neg | seldom |
| | | 35 | M | o | o | o | o | neg | neg | neg | occasional |
| | | 24 | F | o | o | o | o | neg | neg | neg | regular |
| | | 18 | F | o | + | o | o | neg | neg | neg | regular |
| | | 21 | F | o | o | o | (+) | neg | neg | neg | occasional |
| | | 37 | M | o | o | o | (+) | neg | neg | neg | regular |
| | | 20 | F | o | o | o | o | neg | neg | neg | regular |
| 150 healthy blood donors (serum) | positive slightly positive | N/A | N/A | 1.5% 4.5% | 0% 4.5% | 1.5% 0% | 1.5% 12% | N/A | neg | neg | none |

BoDV-1, borna disease virus;
CSF, liquor;
ELISA, enzyme-linked immunosorbent assay;
IFAT, immunofluorescence antibody test;
VSBV-1, variegated squirrel bornavirus 1;
N/A, not available;
+, highly positive;
(+), slightly positive;
o, no immunoblot reaction.
*The results were obtained by densitometry using the EUROLineScan software and transferred into semiquantitative categories (negative, o: 0-13; slightly positive, (+): 14-20; positive, +: 21-255).
§Final OD values for a serum dilution of 1:400 were considered positive when the average OD exceeded the average OD plus three times the standard deviation obtained with negative control samples.
The IgG end point titre is defined as the reciprocal highest analyte dilution which yields a positive immunofluorescence signal.

Serological Testing of the Animal Keepers

Sera from all fourteen animal keepers were ELISA-, immunofluorescence- and immunoblot-tested. Six animal keepers had contact on a regular basis with the variegated squirrels, and five of them had contact on an occasional basis. The remaining individuals had contact only rarely. Judging from the immunoblot, six of the fourteen sera reacted positively or slightly positively with VSBV-1-N, and four with BoDV-1-N, but none with the corresponding P antigen. The immunofluorescence test showed low titres in two cases, whereas ELISA results were negative. The serological reactivity did not correlate with the reported intensity of contact with the squirrels. According to the immunoblot, 13.5%, 4.5%, 1.5% and 6% of the blood donors reacted positively or slightly positively with VSBV-1-N, BoDV-1-N, VSBV-1-P and BoDV-1-P antigen, respectively. One of the blood donors reacted with more than one bornavirus antigen.

The invention claimed is:

1. A method for diagnosing a limbic encephalitis, paraneoplastic neurological syndrome (PNS), encephaloymyelitis, leukoencephalopathy, retinitis or optic atrophy, comprising:
   detecting a bornavirus in a sample from a human or animal by:
   incubating a sample from a human or animal having or suspected of having limbic encephalitis, PNS, encephaloymyelitis, leukoencephalopathy, retinitis, or optic atrophy, with a carrier comprising at least one of each of:
   1. borna disease virus-1 protein (BoDV) or variants thereof having 95% amino acid identity to amino acids 1-376 of SEQ ID NO: 4 or 1-203 of SEQ ID NO: 5, and
   2. variegated squirrel bornavirus 1 protein (VSBV) or variants thereof having 95% amino acid identity to amino acids 1-376 of SEQ ID NO: 1 or 1-204 of SEQ ID NO: 3,
   wherein the BoDV or variants thereof and the VSBV or variants thereof are bonded to the carrier;
   detecting a binding between an antibody against a bornavirus-specific polypeptide and said polypeptide in the sample.

2. A method for prognosticating neurological post-transplantation complications or for screening organ donors or donor organs, comprising:
   detecting a bornavirus in a sample from a human or animal by:
   incubating a sample from a human or animal having or suspected of having limbic encephalitis, PNS, encephaloymyelitis, leukoencephalopathy, retinitis, or optic atrophy, with a carrier comprising at least one of each of:
   1. borna disease virus-1 protein (BoDV) or variants thereof having 95% amino acid identity to amino acids 1-376 of SEQ ID NO: 4 or 1-203 of SEQ ID NO: 5, and
   2. variegated squirrel bornavirus 1 protein (VSBV) or variants thereof having 95% amino acid identity to amino acids 1-376 of SEQ ID NO: 1 or 1-204 of SEQ ID NO: 3,
   wherein the BoDV or variants thereof and the VSBV or variants thereof are bonded to the carrier;

detecting a binding between an antibody against a bornavirus-specific polypeptide and said polypeptide in the sample.

3. A method for differentiating between an autoimmune encephalitis and an encephalitis caused by infection, comprising:
  detecting a bornavirus in a sample from a human or animal by:
    incubating a sample from a human or animal having or suspected of having limbic encephalitis, PNS, encephaloymyelitis, leukoencephalopathy, retinitis, or optic atrophy, with a carrier comprising at least one of each of:
      1. borna disease virus-1 protein (BoDV) or variants thereof having 95% amino acid identity to amino acids 1-376 of SEQ ID NO: 4 or 1-203 of SEQ ID NO: 5, and
      2. variegated squirrel bornavirus 1 protein (VSBV) or variants thereof having 95% amino acid identity to amino acids 1-376 of SEQ ID NO: 1 or 1-204 of SEQ ID NO: 3,
    wherein the BoDV or variants thereof and the VSBV or variants thereof are bonded to the carrier;
  detecting a binding between an antibody against a bornavirus-specific polypeptide and said polypeptide in the sample.

4. The method according to claim 1, wherein the bornavirus-specific polypeptide in the sample is selected from the group consisting of a BoDV-1 nucleoprotein (N) and BoDV-1 phosphoprotein (P).

5. The method according to claim 4, wherein the sample is contacted to the carrier to capture an antibody against at least one polypeptide selected from the group consisting of BoDV-1-N, BoDV-1-P, VSBV-p40 (VSBV-N), and VSBV phosphoprotein (VSBV P).

6. The method according to claim 5, wherein a captured antibody is detected by enzyme activity, fluorescence or chemiluminescence.

7. The method according to claim 5, wherein the carrier is selected from the group consisting of a membrane-based immunoblot, one or more than one bead, a biochip arranged for immunofluorescence, and an ELISA microtiter plate.

8. The method of claim 1, wherein the bornavirus is selected from the group consisting of mammalian 2 bornavirus and mammalian 1 bornavirus.

9. The method according to claim 2, wherein the bornavirus-specific polypeptide in the sample is selected from the group consisting of an N and P protein of the bornavirus.

10. The method according to claim 3, wherein the bornavirus-specific polypeptide in the sample is selected from the group consisting of an N and P protein of the bornavirus.

* * * * *